(12) United States Patent
Robertson et al.

(10) Patent No.: US 8,579,928 B2
(45) Date of Patent: Nov. 12, 2013

(54) OUTER SHEATH AND BLADE ARRANGEMENTS FOR ULTRASONIC SURGICAL INSTRUMENTS

(75) Inventors: Galen C. Robertson, Cincinnati, OH (US); Matthew C. Miller, Cincinnati, OH (US); Prasanna Malaviya, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 317 days.

(21) Appl. No.: 12/703,885

(22) Filed: Feb. 11, 2010

(65) Prior Publication Data

US 2011/0196403 A1    Aug. 11, 2011

(51) Int. Cl.
A61B 17/32    (2006.01)
(52) U.S. Cl.
USPC .............................................. 606/169
(58) Field of Classification Search
USPC ................... 606/167, 169–171, 180; 604/22; 600/562–568
See application file for complete search history.

(56) References Cited

U.S. PATENT DOCUMENTS

| | | |
|---|---|---|
| 969,528 A | 9/1910 | Disbrow |
| 1,570,025 A | 1/1926 | Young |
| 2,704,333 A | 3/1955 | Calosi et al. |
| 2,736,960 A | 3/1956 | Armstrong |
| 2,849,788 A | 9/1958 | Creek |
| RE25,033 E | 8/1961 | Balamuth et al. |
| 3,015,961 A | 1/1962 | Roney |
| 3,513,848 A | 5/1970 | Winston et al. |
| 3,526,219 A | 9/1970 | Balamuth |
| 3,614,484 A | 10/1971 | Shoh |
| 3,636,943 A | 1/1972 | Balamuth |
| 3,776,238 A | 12/1973 | Peyman et al. |
| 3,805,787 A | 4/1974 | Banko |
| 3,830,098 A | 8/1974 | Antonevich |
| 3,854,737 A | 12/1974 | Gilliam, Sr. |
| 3,862,630 A | 1/1975 | Balamuth |
| 3,900,823 A | 8/1975 | Sokal et al. |
| 3,918,442 A | 11/1975 | Nikolaev et al. |

(Continued)

FOREIGN PATENT DOCUMENTS

| | | |
|---|---|---|
| CN | 1634601 A | 7/2005 |
| CN | 1640365 A | 7/2005 |

(Continued)

OTHER PUBLICATIONS

*Technology Overview*, printed from www.harmonicscalpel.com, Internet site, website accessed on Jun. 13, 2007, (3 pages).

(Continued)

*Primary Examiner* — Ryan Severson

(57) ABSTRACT

In various embodiments, a surgical instrument for operation in an aqueous environment is provided. In at least one embodiment, the surgical instrument may include a hollow sheath, a blade disposed at least partially within the hollow sheath and extending through an opening in the sheath, and at least one ultrasonic transducer operably coupled to the blade. The blade may include a polygonal cross-sectional shape and the tip may project away from the sheath's longitudinal axis. In another embodiment, the surgical instrument may include a blade with suction disposed therethrough and at least one ultrasonic transducer operably coupled to the blade. The blade may include a cutting edge that is positioned over a blade opening. Also, the cutting edge may project away from the blade's longitudinal axis.

21 Claims, 8 Drawing Sheets

(56) References Cited

U.S. PATENT DOCUMENTS

| | | | |
|---|---|---|---|
| 3,946,738 | A | 3/1976 | Newton et al. |
| 3,955,859 | A | 5/1976 | Stella et al. |
| 3,956,826 | A | 5/1976 | Perdreaux, Jr. |
| 4,156,187 | A | 5/1979 | Murry et al. |
| 4,188,927 | A | 2/1980 | Harris |
| 4,200,106 | A | 4/1980 | Douvas et al. |
| 4,306,570 | A | 12/1981 | Matthews |
| 4,445,063 | A | 4/1984 | Smith |
| 4,491,132 | A | 1/1985 | Aikins |
| 4,504,264 | A | 3/1985 | Kelman |
| 4,574,615 | A | 3/1986 | Bower et al. |
| 4,617,927 | A | 10/1986 | Manes |
| 4,633,119 | A | 12/1986 | Thompson |
| 4,634,420 | A | 1/1987 | Spinosa et al. |
| 4,640,279 | A | 2/1987 | Beard |
| 4,649,919 | A | 3/1987 | Thimsen et al. |
| 4,708,127 | A | 11/1987 | Abdelghani |
| 4,712,722 | A | 12/1987 | Hood et al. |
| 4,827,911 | A | 5/1989 | Broadwin et al. |
| 4,832,683 | A | 5/1989 | Idemoto et al. |
| 4,838,853 | A | 6/1989 | Parisi |
| 4,850,354 | A | 7/1989 | McGurk-Burleson et al. |
| 4,865,159 | A | 9/1989 | Jamison |
| 4,896,009 | A | 1/1990 | Pawlowski |
| 4,903,696 | A | 2/1990 | Stasz et al. |
| 4,922,902 | A | 5/1990 | Wuchinich et al. |
| 4,965,532 | A | 10/1990 | Sakurai |
| 4,979,952 | A | 12/1990 | Kubota et al. |
| 4,981,756 | A | 1/1991 | Rhandhawa |
| 5,026,387 | A | 6/1991 | Thomas |
| 5,109,819 | A | 5/1992 | Custer et al. |
| 5,112,300 | A | 5/1992 | Ureche |
| 5,123,903 | A | 6/1992 | Quaid et al. |
| 5,126,618 | A | 6/1992 | Takahashi et al. |
| 5,162,044 | A | 11/1992 | Gahn et al. |
| 5,163,537 | A | 11/1992 | Radev |
| 5,167,725 | A | 12/1992 | Clark et al. |
| D332,660 | S | 1/1993 | Rawson et al. |
| 5,176,677 | A | 1/1993 | Wuchinich |
| 5,176,695 | A | 1/1993 | Dulebohn |
| 5,184,605 | A | 2/1993 | Greszykowski |
| 5,188,102 | A | 2/1993 | Idemoto et al. |
| 5,213,569 | A | 5/1993 | Davis |
| 5,221,282 | A | 6/1993 | Wuchinich |
| 5,226,909 | A | 7/1993 | Evans et al. |
| 5,226,910 | A | 7/1993 | Kajiyama et al. |
| 5,241,236 | A | 8/1993 | Sasaki et al. |
| 5,257,988 | A | 11/1993 | L'Esperance, Jr. |
| 5,261,922 | A | 11/1993 | Hood |
| 5,263,957 | A | 11/1993 | Davison |
| 5,275,609 | A | 1/1994 | Pingleton et al. |
| 5,282,800 | A | 2/1994 | Foshee et al. |
| 5,304,115 | A | 4/1994 | Pflueger et al. |
| D347,474 | S | 5/1994 | Olson |
| 5,322,055 | A | 6/1994 | Davison et al. |
| 5,324,299 | A | 6/1994 | Davison et al. |
| 5,326,342 | A | 7/1994 | Pflueger et al. |
| 5,344,420 | A | 9/1994 | Hilal et al. |
| 5,346,502 | A | 9/1994 | Estabrook et al. |
| 5,353,474 | A | 10/1994 | Good et al. |
| 5,357,164 | A | 10/1994 | Imabayashi et al. |
| 5,357,423 | A | 10/1994 | Weaver et al. |
| 5,366,466 | A | 11/1994 | Christian et al. |
| 5,371,429 | A | 12/1994 | Manna |
| D354,564 | S | 1/1995 | Medema |
| 5,381,067 | A | 1/1995 | Greenstein et al. |
| 5,403,312 | A | 4/1995 | Yates et al. |
| D358,887 | S | 5/1995 | Feinberg |
| 5,411,481 | A | 5/1995 | Allen et al. |
| 5,419,761 | A | 5/1995 | Narayanan et al. |
| 5,421,829 | A | 6/1995 | Olichney et al. |
| 5,438,997 | A | 8/1995 | Sieben et al. |
| 5,449,370 | A | 9/1995 | Vaitekunas |
| 5,471,988 | A | 12/1995 | Fujio et al. |
| 5,483,501 | A | 1/1996 | Park et al. |
| 5,486,162 | A | 1/1996 | Brumbach |
| 5,500,216 | A | 3/1996 | Julian et al. |
| 5,501,654 | A | 3/1996 | Failla et al. |
| 5,505,693 | A | 4/1996 | Mackool |
| 5,507,738 | A | 4/1996 | Ciervo |
| 5,527,331 | A | 6/1996 | Kresch et al. |
| 5,562,609 | A | 10/1996 | Brumbach |
| 5,562,610 | A | 10/1996 | Brumbach |
| 5,577,654 | A | 11/1996 | Bishop |
| 5,601,601 | A | 2/1997 | Tal et al. |
| 5,603,773 | A | 2/1997 | Campbell |
| 5,607,436 | A | 3/1997 | Pratt et al. |
| 5,618,492 | A | 4/1997 | Auten et al. |
| 5,628,760 | A | 5/1997 | Knoepfler |
| 5,630,420 | A | 5/1997 | Vaitekunas |
| D381,077 | S | 7/1997 | Hunt |
| 5,651,780 | A | 7/1997 | Jackson et al. |
| 5,653,713 | A | 8/1997 | Michelson |
| 5,669,922 | A | 9/1997 | Hood |
| 5,674,235 | A | 10/1997 | Parisi |
| 5,690,269 | A | 11/1997 | Bolanos et al. |
| 5,694,936 | A | 12/1997 | Fujimoto et al. |
| 5,713,896 | A | 2/1998 | Nardella |
| 5,730,752 | A * | 3/1998 | Alden et al. .................. 606/180 |
| 5,733,074 | A | 3/1998 | Stöck et al. |
| 5,741,226 | A | 4/1998 | Strukel et al. |
| 5,792,135 | A | 8/1998 | Madhani et al. |
| 5,792,165 | A | 8/1998 | Klieman et al. |
| 5,808,396 | A | 9/1998 | Boukhny |
| 5,810,859 | A | 9/1998 | DiMatteo et al. |
| 5,817,084 | A | 10/1998 | Jensen |
| 5,817,119 | A | 10/1998 | Klieman et al. |
| 5,827,323 | A | 10/1998 | Klieman et al. |
| 5,828,160 | A | 10/1998 | Sugishita |
| 5,833,696 | A | 11/1998 | Whitfield et al. |
| 5,836,897 | A | 11/1998 | Sakurai et al. |
| 5,843,109 | A | 12/1998 | Mehta et al. |
| 5,878,193 | A | 3/1999 | Wang et al. |
| 5,879,364 | A | 3/1999 | Bromfield et al. |
| 5,883,615 | A | 3/1999 | Fago et al. |
| 5,893,835 | A | 4/1999 | Witt et al. |
| 5,897,523 | A | 4/1999 | Wright et al. |
| 5,897,569 | A | 4/1999 | Kellogg et al. |
| 5,906,628 | A * | 5/1999 | Miyawaki et al. ............. 606/169 |
| 5,911,699 | A | 6/1999 | Anis et al. |
| 5,935,143 | A | 8/1999 | Hood |
| 5,935,144 | A | 8/1999 | Estabrook |
| 5,938,633 | A | 8/1999 | Beaupre |
| 5,944,718 | A | 8/1999 | Austin et al. |
| 5,944,737 | A | 8/1999 | Tsonton et al. |
| 5,954,736 | A | 9/1999 | Bishop et al. |
| 5,954,746 | A | 9/1999 | Holthaus et al. |
| 5,957,882 | A | 9/1999 | Nita et al. |
| 5,957,943 | A | 9/1999 | Vaitekunas |
| 5,968,007 | A | 10/1999 | Simon et al. |
| 5,968,060 | A | 10/1999 | Kellogg |
| D416,089 | S | 11/1999 | Barton et al. |
| 5,980,510 | A | 11/1999 | Tsonton et al. |
| 5,989,274 | A | 11/1999 | Davison et al. |
| 5,989,275 | A | 11/1999 | Estabrook et al. |
| 5,993,972 | A | 11/1999 | Reich et al. |
| 6,024,741 | A | 2/2000 | Williamson, IV et al. |
| 6,027,515 | A | 2/2000 | Cimino |
| 6,033,375 | A | 3/2000 | Brumbach |
| 6,050,943 | A | 4/2000 | Slayton et al. |
| 6,051,010 | A | 4/2000 | DiMatteo et al. |
| 6,056,735 | A | 5/2000 | Okada et al. |
| 6,063,098 | A | 5/2000 | Houser et al. |
| 6,066,132 | A | 5/2000 | Chen et al. |
| 6,066,151 | A | 5/2000 | Miyawaki et al. |
| 6,068,647 | A | 5/2000 | Witt et al. |
| 6,077,285 | A | 6/2000 | Boukhny |
| 6,083,191 | A | 7/2000 | Rose |
| 6,086,584 | A | 7/2000 | Miller |
| 6,090,120 | A | 7/2000 | Wright et al. |
| 6,109,500 | A | 8/2000 | Alli et al. |
| 6,110,127 | A | 8/2000 | Suzuki |
| 6,113,594 | A | 9/2000 | Savage |
| 6,117,152 | A | 9/2000 | Huitema |

(56) References Cited

U.S. PATENT DOCUMENTS

| | | |
|---|---|---|
| 6,126,629 A | 10/2000 | Perkins |
| 6,129,735 A | 10/2000 | Okada et al. |
| 6,132,368 A | 10/2000 | Cooper |
| 6,139,320 A | 10/2000 | Hahn |
| 6,139,561 A | 10/2000 | Shibata et al. |
| 6,142,615 A | 11/2000 | Qiu et al. |
| 6,147,560 A | 11/2000 | Erhage et al. |
| 6,152,902 A | 11/2000 | Christian et al. |
| 6,159,160 A | 12/2000 | Hsei et al. |
| 6,159,175 A | 12/2000 | Strukel et al. |
| 6,165,150 A | 12/2000 | Banko |
| 6,204,592 B1 | 3/2001 | Hur |
| 6,206,844 B1 | 3/2001 | Reichel et al. |
| 6,210,403 B1 | 4/2001 | Klicek |
| 6,214,023 B1 | 4/2001 | Whipple et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,252,110 B1 | 6/2001 | Uemura et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,340,352 B1 | 1/2002 | Okada et al. |
| 6,352,532 B1 | 3/2002 | Kramer et al. |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,387,109 B1 | 5/2002 | Davison et al. |
| 6,388,657 B1 | 5/2002 | Natoli |
| 6,391,042 B1 | 5/2002 | Cimino |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,524,251 B2 | 2/2003 | Rabiner et al. |
| 6,524,316 B1 | 2/2003 | Nicholson et al. |
| 6,527,736 B1 * | 3/2003 | Attinger et al. ................ 604/43 |
| 6,533,784 B2 | 3/2003 | Truckai et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,561,983 B2 | 5/2003 | Cronin et al. |
| 6,572,632 B2 | 6/2003 | Zisterer et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,610,059 B1 | 8/2003 | West, Jr. |
| 6,616,450 B2 | 9/2003 | Mossle et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,656,177 B2 | 12/2003 | Truckai et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,899 B2 | 1/2004 | Wiener et al. |
| 6,682,544 B2 | 1/2004 | Mastri et al. |
| 6,689,146 B1 | 2/2004 | Himes |
| 6,716,215 B1 | 4/2004 | David et al. |
| 6,731,047 B2 | 5/2004 | Kauf et al. |
| 6,733,506 B1 | 5/2004 | McDevitt et al. |
| 6,762,535 B2 | 7/2004 | Take et al. |
| 6,770,072 B1 | 8/2004 | Truckai et al. |
| 6,773,443 B2 | 8/2004 | Truwit et al. |
| 6,773,444 B2 | 8/2004 | Messerly |
| 6,783,524 B2 | 8/2004 | Anderson et al. |
| 6,786,382 B1 | 9/2004 | Hoffman |
| 6,786,383 B2 | 9/2004 | Stegelmann |
| 6,790,216 B1 | 9/2004 | Ishikawa |
| D496,997 S | 10/2004 | Dycus et al. |
| 6,802,843 B2 | 10/2004 | Truckai et al. |
| 6,827,712 B2 | 12/2004 | Tovey et al. |
| 6,828,712 B2 | 12/2004 | Battaglin et al. |
| 6,869,439 B2 | 3/2005 | White et al. |
| 6,875,220 B2 | 4/2005 | Du et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,923,804 B2 | 8/2005 | Eggers et al. |
| 6,926,716 B2 | 8/2005 | Baker et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,677 B2 | 9/2005 | Nita et al. |
| 6,945,981 B2 | 9/2005 | Donofrio et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 7,001,335 B2 | 2/2006 | Adachi et al. |
| 7,011,657 B2 | 3/2006 | Truckai et al. |
| 7,033,357 B2 | 4/2006 | Baxter et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |
| 7,101,378 B2 | 9/2006 | Salameh et al. |
| 7,108,695 B2 | 9/2006 | Witt et al. |
| 7,112,201 B2 | 9/2006 | Truckai et al. |
| D531,311 S | 10/2006 | Guerra et al. |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,135,018 B2 | 11/2006 | Ryan et al. |
| 7,135,030 B2 | 11/2006 | Schwemberger et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,299 B2 | 1/2007 | Baily |

(56) References Cited

U.S. PATENT DOCUMENTS

| | | |
|---|---|---|
| 7,163,548 B2 | 1/2007 | Stulen et al. |
| 7,169,146 B2 | 1/2007 | Truckai et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| D541,418 S | 4/2007 | Schechter et al. |
| 7,204,820 B2 | 4/2007 | Akahoshi |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,273,483 B2 | 9/2007 | Wiener et al. |
| 7,285,895 B2 | 10/2007 | Beaupré |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,331,410 B2 | 2/2008 | Yong et al. |
| 7,353,068 B2 | 4/2008 | Tanaka et al. |
| 7,354,440 B2 | 4/2008 | Truckai et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| D576,725 S | 9/2008 | Shumer et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,488,285 B2 | 2/2009 | Honda et al. |
| 7,494,468 B2 | 2/2009 | Rabiner et al. |
| 7,503,893 B2 | 3/2009 | Kucklick |
| 7,503,895 B2 * | 3/2009 | Rabiner et al. ............... 600/439 |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,549,564 B2 | 6/2009 | Boudreaux |
| 7,559,450 B2 | 7/2009 | Wales et al. |
| 7,567,012 B2 | 7/2009 | Namikawa |
| 7,578,820 B2 | 8/2009 | Moore et al. |
| 7,654,431 B2 | 2/2010 | Hueil et al. |
| 7,665,647 B2 | 2/2010 | Shelton, IV et al. |
| 7,670,334 B2 | 3/2010 | Hueil et al. |
| 7,674,263 B2 | 3/2010 | Ryan |
| 7,691,098 B2 | 4/2010 | Wallace et al. |
| 7,713,202 B2 | 5/2010 | Boukhny et al. |
| 7,714,481 B2 | 5/2010 | Sakai |
| D618,797 S | 6/2010 | Price et al. |
| 7,751,115 B2 | 7/2010 | Song |
| D621,503 S | 8/2010 | Otten et al. |
| 7,770,774 B2 | 8/2010 | Mastri et al. |
| 7,770,775 B2 | 8/2010 | Shelton, IV et al. |
| 7,780,054 B2 | 8/2010 | Wales |
| 7,780,659 B2 | 8/2010 | Okada et al. |
| 7,784,662 B2 | 8/2010 | Wales et al. |
| 7,798,386 B2 | 9/2010 | Schall et al. |
| 7,803,152 B2 | 9/2010 | Honda et al. |
| 7,806,891 B2 | 10/2010 | Nowlin et al. |
| 7,810,693 B2 | 10/2010 | Broehl et al. |
| D627,066 S | 11/2010 | Romero |
| 7,824,401 B2 | 11/2010 | Manzo et al. |
| 7,837,699 B2 | 11/2010 | Yamada et al. |
| 7,846,155 B2 | 12/2010 | Houser et al. |
| 7,854,735 B2 | 12/2010 | Houser et al. |
| D631,155 S | 1/2011 | Peine et al. |
| 7,861,906 B2 | 1/2011 | Doll et al. |
| 7,876,030 B2 | 1/2011 | Taki et al. |
| D631,965 S | 2/2011 | Price et al. |
| 7,892,606 B2 | 2/2011 | Thies et al. |
| 7,901,423 B2 | 3/2011 | Stulen et al. |
| 7,905,881 B2 | 3/2011 | Masuda et al. |
| 7,922,651 B2 | 4/2011 | Yamada et al. |
| D637,288 S | 5/2011 | Houghton |
| D638,540 S | 5/2011 | Ijiri et al. |
| 7,959,050 B2 | 6/2011 | Smith et al. |
| 7,959,626 B2 | 6/2011 | Hong et al. |
| 7,976,544 B2 | 7/2011 | McClurken et al. |
| 7,998,157 B2 | 8/2011 | Culp et al. |
| 8,038,693 B2 | 10/2011 | Allen |
| 8,061,014 B2 | 11/2011 | Smith et al. |
| 8,089,197 B2 | 1/2012 | Rinner et al. |
| 8,152,825 B2 | 4/2012 | Madan et al. |
| 8,157,145 B2 | 4/2012 | Shelton, IV et al. |
| 8,162,966 B2 | 4/2012 | Connor et al. |
| 8,177,800 B2 | 5/2012 | Spitz et al. |
| 8,182,502 B2 | 5/2012 | Stulen et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,253,303 B2 | 8/2012 | Giordano et al. |
| 8,287,485 B2 | 10/2012 | Kimura et al. |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156466 A1 | 10/2002 | Sakurai et al. |
| 2002/0156493 A1 | 10/2002 | Houser et al. |
| 2003/0036705 A1 | 2/2003 | Hare et al. |
| 2003/0055443 A1 | 3/2003 | Spotnitz |
| 2003/0204199 A1 | 10/2003 | Novak et al. |
| 2003/0212332 A1 | 11/2003 | Fenton et al. |
| 2003/0212422 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0097919 A1 | 5/2004 | Wellman et al. |
| 2004/0097996 A1 | 5/2004 | Rabiner et al. |
| 2004/0176686 A1 | 9/2004 | Hare et al. |
| 2004/0199193 A1 | 10/2004 | Hayashi et al. |
| 2004/0204728 A1 | 10/2004 | Haefner |
| 2004/0260300 A1 | 12/2004 | Gorensek et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0192610 A1 | 9/2005 | Houser et al. |
| 2005/0209620 A1 | 9/2005 | Du et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0063130 A1 | 3/2006 | Hayman et al. |
| 2006/0066181 A1 | 3/2006 | Bromfield et al. |
| 2006/0079876 A1 | 4/2006 | Houser et al. |
| 2006/0079878 A1 | 4/2006 | Houser |
| 2006/0084963 A1 | 4/2006 | Messerly |
| 2006/0095046 A1 * | 5/2006 | Trieu et al. ............... 606/99 |
| 2006/0190034 A1 | 8/2006 | Nishizawa et al. |

(56) References Cited

U.S. PATENT DOCUMENTS

| | | |
|---|---|---|
| 2006/0206115 A1* | 9/2006 | Schomer et al. ............... 606/79 |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2006/0264809 A1 | 11/2006 | Hansmann et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0173872 A1 | 7/2007 | Neuenfeldt |
| 2007/0185380 A1 | 8/2007 | Kucklick |
| 2007/0219481 A1 | 9/2007 | Babaev |
| 2007/0239028 A1 | 10/2007 | Houser et al. |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0082098 A1 | 4/2008 | Tanaka et al. |
| 2008/0125768 A1 | 5/2008 | Tahara et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234708 A1 | 9/2008 | Houser et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0243106 A1 | 10/2008 | Coe et al. |
| 2008/0245371 A1 | 10/2008 | Gruber |
| 2008/0249553 A1 | 10/2008 | Gruber et al. |
| 2008/0262490 A1 | 10/2008 | Williams |
| 2008/0281200 A1 | 11/2008 | Voic et al. |
| 2008/0287948 A1 | 11/2008 | Newton et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0105750 A1 | 4/2009 | Price et al. |
| 2009/0118802 A1 | 5/2009 | Mioduski et al. |
| 2009/0138006 A1 | 5/2009 | Bales et al. |
| 2009/0143795 A1 | 6/2009 | Robertson |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0143806 A1 | 6/2009 | Witt et al. |
| 2009/0149801 A1 | 6/2009 | Crandall et al. |
| 2009/0270853 A1 | 10/2009 | Yachi et al. |
| 2009/0270899 A1 | 10/2009 | Carusillo et al. |
| 2009/0318945 A1 | 12/2009 | Yoshimine et al. |
| 2009/0327715 A1 | 12/2009 | Smith et al. |
| 2010/0004668 A1 | 1/2010 | Smith et al. |
| 2010/0004669 A1 | 1/2010 | Smith et al. |
| 2010/0016785 A1 | 1/2010 | Takuma |
| 2010/0030248 A1 | 2/2010 | Palmer et al. |
| 2010/0036370 A1 | 2/2010 | Mirel et al. |
| 2010/0036405 A1 | 2/2010 | Giordano et al. |
| 2010/0069940 A1 | 3/2010 | Miller et al. |
| 2010/0158307 A1 | 6/2010 | Kubota et al. |
| 2010/0179577 A1 | 7/2010 | Houser |
| 2010/0187283 A1 | 7/2010 | Crainich et al. |
| 2010/0193567 A1 | 8/2010 | Scheib et al. |
| 2010/0228264 A1 | 9/2010 | Robinson et al. |
| 2010/0234906 A1 | 9/2010 | Koh |
| 2010/0268211 A1 | 10/2010 | Manwaring et al. |
| 2010/0298743 A1 | 11/2010 | Nield et al. |
| 2010/0298851 A1 | 11/2010 | Nield |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2011/0009850 A1 | 1/2011 | Main et al. |
| 2011/0015627 A1 | 1/2011 | DiNardo et al. |
| 2011/0015631 A1 | 1/2011 | Wiener et al. |
| 2011/0015660 A1 | 1/2011 | Wiener et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087256 A1 | 4/2011 | Wiener et al. |
| 2011/0196286 A1 | 8/2011 | Robertson et al. |
| 2011/0196287 A1 | 8/2011 | Robertson et al. |
| 2011/0196398 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196404 A1 | 8/2011 | Dietz et al. |
| 2011/0196405 A1 | 8/2011 | Dietz |
| 2011/0288452 A1 | 11/2011 | Houser et al. |
| 2012/0029546 A1 | 2/2012 | Robertson |
| 2012/0059289 A1 | 3/2012 | Nield et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0083783 A1 | 4/2012 | Davison et al. |
| 2012/0083784 A1 | 4/2012 | Davison et al. |
| 2012/0132450 A1 | 5/2012 | Timm et al. |
| 2012/0138660 A1 | 6/2012 | Shelton, IV |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0203257 A1 | 8/2012 | Stulen et al. |
| 2012/0205421 A1 | 8/2012 | Shelton, IV |
| 2012/0210223 A1 | 8/2012 | Eppolito |
| 2012/0211546 A1 | 8/2012 | Shelton, IV |
| 2012/0259353 A1 | 10/2012 | Houser et al. |
| 2012/0265196 A1 | 10/2012 | Turner et al. |
| 2012/0269676 A1 | 10/2012 | Houser et al. |
| 2012/0289984 A1 | 11/2012 | Houser et al. |
| 2012/0310262 A1 | 12/2012 | Messerly et al. |

(56) References Cited

U.S. PATENT DOCUMENTS

| | | |
|---|---|---|
| 2012/0310263 A1 | 12/2012 | Messerly et al. |
| 2012/0310264 A1 | 12/2012 | Messerly et al. |
| 2012/0323265 A1 | 12/2012 | Stulen |
| 2013/0012970 A1 | 1/2013 | Houser |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0123782 A1 | 5/2013 | Trees et al. |

FOREIGN PATENT DOCUMENTS

| | | |
|---|---|---|
| CN | 1694649 A | 11/2005 |
| CN | 1922563 A | 2/2007 |
| CN | 1951333 A | 4/2007 |
| CN | 101040799 A | 9/2007 |
| EP | 0171967 A2 | 2/1986 |
| EP | 0443256 A1 | 8/1991 |
| EP | 0456470 A1 | 11/1991 |
| EP | 0482195 B1 | 4/1992 |
| EP | 0482195 B1 | 1/1996 |
| EP | 0612570 B1 | 6/1997 |
| EP | 0908148 B1 | 1/2002 |
| EP | 0908155 B1 | 6/2003 |
| EP | 1199044 B1 | 12/2005 |
| EP | 1199043 B1 | 3/2006 |
| EP | 1433425 B1 | 6/2006 |
| EP | 1844720 A1 | 10/2007 |
| EP | 1862133 A1 | 12/2007 |
| EP | 1199045 B1 | 6/2008 |
| EP | 1974771 A1 | 10/2008 |
| EP | 1498082 B1 | 12/2008 |
| EP | 1832259 B1 | 6/2009 |
| EP | 2074959 A1 | 7/2009 |
| EP | 2298154 A2 | 3/2011 |
| GB | 2032221 A | 4/1980 |
| GB | 2379878 B | 11/2004 |
| GB | 2447767 B | 8/2011 |
| JP | 62-2292153 A | 12/1987 |
| JP | 63-315049 A | 12/1988 |
| JP | 02-71510 U | 5/1990 |
| JP | 04-25707 U | 2/1992 |
| JP | 4-30508 U | 3/1992 |
| JP | 6-104503 A | 4/1994 |
| JP | 6-507081 A | 8/1994 |
| JP | H 7-508910 A | 10/1995 |
| JP | 7-308323 A | 11/1995 |
| JP | 8-24266 A | 1/1996 |
| JP | 8-275951 A | 10/1996 |
| JP | H 09-503146 A | 3/1997 |
| JP | 10-295700 A | 11/1998 |
| JP | 11-253451 A | 9/1999 |
| JP | 2000-041991 A | 2/2000 |
| JP | 2000-070279 A | 3/2000 |
| JP | 2001-309925 A | 11/2001 |
| JP | 2002-186901 A | 7/2002 |
| JP | 2002-263579 A | 9/2002 |
| JP | 2003-510158 A | 3/2003 |
| JP | 2003-126110 A | 5/2003 |
| JP | 2003-310627 A | 5/2003 |
| JP | 2003-339730 A | 12/2003 |
| JP | 2005027026 A | 1/2005 |
| JP | 2005-066316 A | 3/2005 |
| JP | 2005-074088 A | 3/2005 |
| JP | 2005-534451 A | 11/2005 |
| JP | 2006-158525 A | 6/2006 |
| JP | 2006217716 A | 8/2006 |
| JP | 2008-508065 A | 3/2008 |
| JP | 2008-119250 A | 5/2008 |
| JP | 2009-511206 A | 3/2009 |
| WO | WO 92/22259 A2 | 12/1992 |
| WO | WO 93/14708 A1 | 8/1993 |
| WO | WO 94/21183 A1 | 9/1994 |
| WO | WO 95/09572 A1 | 4/1995 |
| WO | WO 98/26739 A1 | 6/1998 |
| WO | WO 98/37815 A1 | 9/1998 |
| WO | WO 01/54590 A1 | 8/2001 |
| WO | WO 01/95810 A2 | 12/2001 |
| WO | WO 2004/037095 A2 | 5/2004 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/129465 A1 | 12/2006 |
| WO | WO 2007/008710 A2 | 1/2007 |
| WO | WO 2007/047531 A2 | 4/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/130793 A1 | 10/2008 |
| WO | WO 2009/018406 A2 | 2/2009 |
| WO | WO 2009/027065 A1 | 3/2009 |
| WO | WO 2011/144911 A1 | 11/2011 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,893, filed Feb. 11, 2010.
U.S. Appl. No. 12/703,899, filed Feb. 11, 2010.
International Search Report for PCT/US2011/024209, Oct. 14, 2011 included in PCT Publication No. WO 2011/100338 A3 (6 pages).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
U.S. Appl. No. 29/404,676, filed Oct. 24, 2011.
U.S. Appl. No. 13/448,175, filed Apr. 16, 2012.
U.S. Appl. No. 13/151,181, filed Jun. 2, 2011.

(56) References Cited

OTHER PUBLICATIONS

U.S. Appl. No. 13/369,561, filed Feb. 9, 2012.
U.S. Appl. No. 13/369,569, filed Feb. 9, 2012.
U.S. Appl. No. 13/369,578, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601, filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/545,292, filed Jul. 10, 2012.
U.S. Appl. No. 13/584,020, filed Aug. 13, 2012.
U.S. Appl. No. 13/584,445, filed Aug. 13, 2012.
U.S. Appl. No. 13/584,878, filed Aug. 14, 2012.
U.S. Appl. No. 13/585,124, filed Aug. 14, 2012.
U.S. Appl. No. 13/585,292, filed Aug. 14, 2012.
International Preliminary Report on Patentability for PCT/US2011/024209, Aug. 14, 2012 (9 pages).
U.S. Appl. No. 13/849,627, filed Mar. 25, 2013.

* cited by examiner

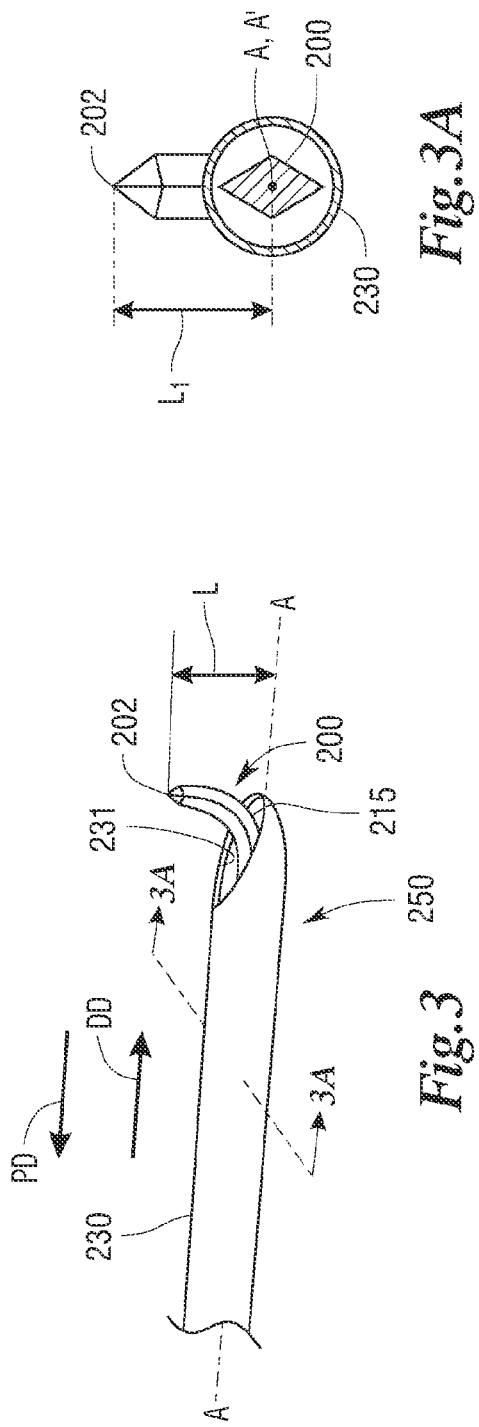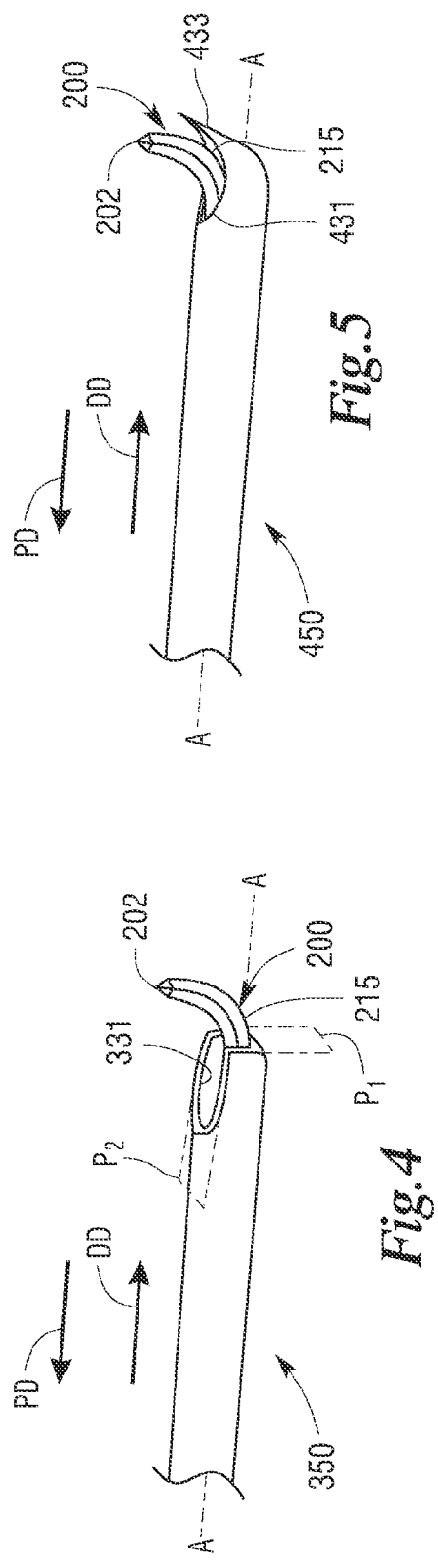

OUTER SHEATH AND BLADE ARRANGEMENTS FOR ULTRASONIC SURGICAL INSTRUMENTS

BACKGROUND

The present disclosure generally relates to ultrasonic surgical systems and, more particularly, to ultrasonic systems that allow surgeons to perform cutting and coagulation of tissue.

Over the years, a variety of different types of non-ultrasonically powered cutters and shaving devices for performing surgical procedures have been developed. Some of these devices employ a rotary cutting instrument and other devices employ a reciprocating cutting member. For example, shavers are widely used in arthroscopic surgery. Arthroscopic surgery involves performing surgery in the joint space. To perform the surgery, the joints are commonly filled with pressurized saline for distention and visualization.

The aforementioned devices generally consist of a power supply, a handpiece, and a single-use end effector. The end effector commonly has an inner and outer tube. The inner tube rotates relative to the outer tube and will cut tissue with its sharpened edges. The inner tube can rotate continuously or oscillate. In addition, such device may employ a suction channel that travels through the interior of the inner tube. For example, U.S. Pat. No. 4,850,354 to McGurk-Burleson, et al., discloses a non-ultrasonically powered surgical cutting instrument that comprises a rotary cutter for cutting material with a shearing action. It employs an inner cutting member which is rotatable within an outer tube.

U.S. Pat. No. 3,776,238 to Peyman et al. discloses an ophthalmic instrument in which tissue is cut by a chopping action set-up by the sharp end of an inner tube moving against the inner surface of the end of an outer tube. U.S. Pat. No. 5,226,910 to Kajiyama et al. discloses another surgical cutting instrument that has an inner member which moves relative to an outer member to cut tissue entering through an aperture in the outer member.

U.S. Pat. No. 4,922,902 to Wuchinich et al. discloses a method and apparatus for endoscopic removal of tissue utilizing an ultrasonic aspirator. The device uses an ultrasonic probe which disintegrates compliant tissue and aspirates it through a narrow orifice. U.S. Pat. No. 4,634,420 to Spinosa et al. discloses an apparatus and method for removing tissue from an animal and includes an elongated instrument having a needle or probe, which is vibrated at an ultrasonic frequency in the lateral direction. The ultrasonic movement of the needle breaks-up the tissue into fragments. Pieces of tissue can be removed from the area of treatment by aspiration through a conduit in the needle. U.S. Pat. No. 3,805,787 to Banko discloses yet another ultrasonic instrument that has a probe that is shielded to narrow the beam of ultrasonic energy radiated from the tip of the probe. In one embodiment the shield extends past the free-end of the probe to prevent the probe from coming into contact with the tissue. U.S. Pat. No. 5,213,569 to Davis discloses a phaco-emulsification needle which focuses the ultrasonic energy. The focusing surfaces can be beveled, curved or faceted. U.S. Pat. No. 6,984,220 to Wuchinich and U.S. Patent Publication No. US 2005/0177184 to Easley disclose ultrasonic tissue dissection systems that provide combined longitudinal and torsional motion through the use of longitudinal-torsional resonators. U.S. Patent Publication no. US 2006/0030797 A1 to Zhou et al. discloses an orthopedic surgical device that has a driving motor for driving an ultrasound transducer and horn. An adapter is provided between the driving motor and transducer for supplying ultrasonic energy signals to the transducer.

While the use of ultrasonically powered surgical instruments provides several advantages over traditional mechanically powered saws, drills, and other instruments, temperature rise in bone and adjacent tissue due to frictional heating at the bone/tissue interface can still be a significant problem. Current arthroscopic surgical tools include punches, reciprocating shavers and radio frequency (RF) devices. Mechanical devices such as punches and shavers create minimal tissue damage, but can sometimes leave behind ragged cut lines, which are undesirable. RF devices can create smoother cut lines and also ablate large volumes of soft tissue; however, they tend to create more tissue damage than mechanical means. Thus, devices which could provide increased cutting precision while forming smooth cutting surfaces without creating excessive tissue damage would be desirable.

The foregoing discussion is intended only to illustrate the present field and should not be taken as a disavowal of claim scope.

SUMMARY

In various embodiments, a surgical instrument is provided. In at least one embodiment, the surgical instrument can comprise a hollow sheath including an opening, a blade disposed at least partially within the hollow sheath and extending through the opening, and at least one ultrasonic transducer operably coupled to the blade. In these embodiments, the hollow sheath can define a longitudinal axis, and the blade can comprise a tip and a cross-sectional shape adjacent to the tip that is a polygon. Moreover, in these embodiments, the tip can project away from the longitudinal axis.

In at least one embodiment, a surgical instrument is provided that can comprise a blade defining a longitudinal axis, a suction port, and at least one ultrasonic transducer operably coupled to the blade. In these embodiments, the blade can comprise a distal end, a lumen, a first opening adjacent to the distal end, and a first cutting edge positioned over the first opening. Further, in these embodiments, the first opening can communicate with the lumen. Additionally, the first cutting edge can project away from the longitudinal axis. Moreover, in these embodiments, the blade is configured to allow suction to be applied from the suction port to the first opening.

In at least one embodiment, a surgical instrument is provided that can comprise a blade defining a longitudinal axis, a suction port, and at least one ultrasonic transducer operably coupled to the blade. In these embodiments, the blade can comprise a distal end, a lumen, a first opening, a first cutting edge positioned over the first opening, a second opening, and a second cutting edge positioned over the second opening. Further, in these embodiments, the first opening and the second opening can communicate with the lumen. Additionally, the first cutting edge and the second cutting edge can project away from the longitudinal axis and the second cutting edge can be proximal to the first cutting edge. Moreover, in these embodiments, the blade is configured to allow suction to be applied from the suction port to the first opening.

BRIEF DESCRIPTION OF THE FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 3 is a perspective view of a distal portion of the surgical instrument of FIG. 2.

FIG. 3A is a cross-sectional view of the distal portion of the surgical instrument of FIG. 2, taken along line 3A-3A in FIG. 3.

FIG. 4 is a perspective view of an alternative embodiment of the distal portion of the surgical instrument of FIG. 2.

FIG. 5 is a perspective view of another alternative embodiment of the distal portion of the surgical instrument of FIG. 2.

DETAILED DESCRIPTION

Figure 1:
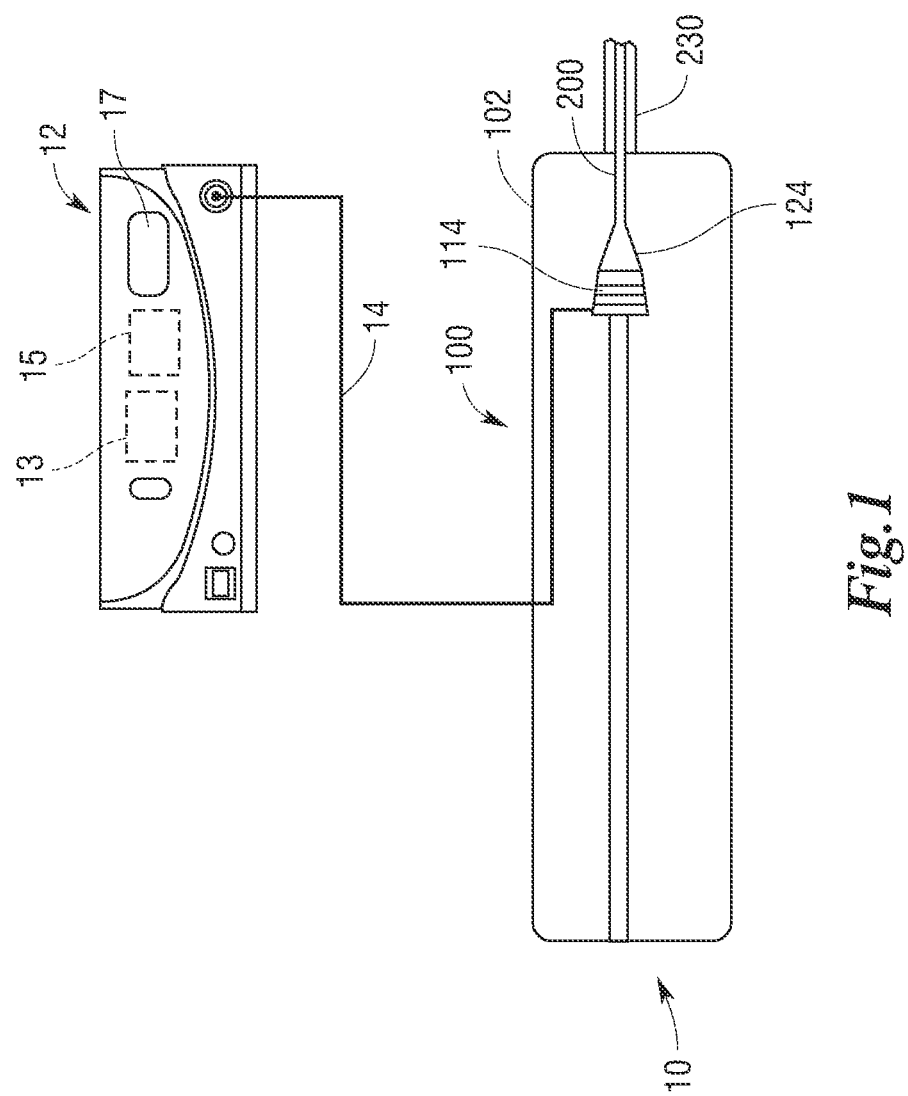
FIG. 1 is a schematic view of a non-limiting embodiment of a surgical control system embodiment.

The owner of the present application also owns the following U.S. Patent Applications that were filed on even date herewith and which are herein incorporated by reference in their respective entireties:

U.S. patent application Ser. No. 12/703,860, entitled ULTRASONICALLY POWERED SURGICAL INSTRUMENTS WITH ROTATING CUTTING IMPLEMENT, now U.S. Patent Application Publication No. 2011/0196286;

U.S. patent application Ser. No. 12/703,864, entitled METHODS OF USING ULTRASONICALLY POWERED SURGICAL INSTRUMENTS WITH ROTATABLE CUTTING IMPLEMENTS, now U.S. Patent Application Publication No. 2011/0196287;

U.S. patent application Ser. No. 12/703,866, entitled SEAL ARRANGEMENTS FOR ULTRASONICALLY POWERED SURGICAL INSTRUMENTS, now U.S. Patent Application Publication No. 2011/0196398;

U.S. patent application Ser. No. 12/703,870, entitled ULTRASONIC SURGICAL INSTRUMENTS WITH ROTATABLE BLADE AND HOLLOW SHEATH ARRANGEMENTS, now U.S. Patent Application Publication No. 2011/0196399;

U.S. patent application Ser. No. 12/703,875, entitled ROTATABLE CUTTING IMPLEMENT ARRANGEMENTS FOR ULTRASONIC SURGICAL INSTRUMENTS, now U.S. Patent Application Publication No. 2011/0196400;

U.S. patent application Ser. No. 12/703,877, entitled ULTRASONIC SURGICAL INSTRUMENTS WITH PARTIALLY ROTATING BLADE AND FIXED PAD ARRANGEMENT, now U.S. Patent Application Publication No. 2011/0196401;

U.S. patent application Ser. No. 12/703,879, entitled DUAL PURPOSE SURGICAL INSTRUMENT FOR CUTTING AND COAGULATING TISSUE, now U.S. Patent Application Publication No. 2011/0196402;

U.S. patent application Ser. No. 12/703,893, entitled ULTRASONIC SURGICAL INSTRUMENTS WITH MOVING CUTTING IMPLEMENT, now U.S. Patent Application Publication No. 2011/0196404; and U.S. patent application Ser. No. 12/703,899, entitled ULTRASONIC SURGICAL INSTRUMENT WITH COMB-LIKE TISSUE TRIMMING DEVICE, now U.S. Patent Application Publication No. 2011/0196405.

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of these embodiments is defined solely by the claims. The features illustrated or described in connection with one embodiment may be combined with the features of other embodiments. Further, where an ordering of steps in a process is indicated, such ordering may be rearranged or the steps may be carried out contemporaneously as desired unless illogical or the listed order is explicitly required. Such modifications and variations are intended to be included within the scope of the appended claims.

In the following description, like reference characters designate like or corresponding parts throughout the several views. Also in the following description, it is to be understood that terms such as "forward," "rearward," "front," "back," "right," "left," "over," "under," "top," "bottom," "upwardly," "downwardly," "proximally," "distally," and the like are words of convenience and are not to be construed as limiting terms. The description below is for the purpose of describing various embodiments and is not intended to limit the appended claims.

Various embodiments are directed to improved ultrasonic surgical systems and instruments configured for effecting tissue dissecting, cutting, and/or coagulation during surgical procedures as well as the cutting implements employed thereby. In one embodiment, an ultrasonic surgical instrument apparatus is configured for use in open surgical procedures, but has applications in other types of surgery, such as laparoscopic, endoscopic, and robotic-assisted procedures.

Versatile use is facilitated by selective use of ultrasonic energy and/or suction applied near and/or through the cutting/coagulation implement.

It will be appreciated that the terms "proximal" and "distal" are used herein with reference to a clinician gripping a handpiece assembly. Thus, an end effector, including, for example, the cutting/coagulation implement, is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

FIG. 1 illustrates in schematic form one embodiment of a surgical system 10 of the present invention. The surgical system 10 may include an ultrasonic generator 12 and an ultrasonic surgical instrument assembly 100 that may include ultrasonic producing components. As will be discussed in further detail below, the ultrasonic generator 12 may be connected by a cable 14 to an ultrasonic transducer assembly 114 in a housing portion 102 of the surgical instrument assembly 100. The transducer assembly 114 may include one or more ultrasonic transducers capable of producing ultrasonic vibrations. Further, attached to the ultrasonic transducer assembly 114 may be a horn 124 for amplifying and/or focusing ultrasonic motions created by the transducer assembly 114. Coupled to the horn 124 may be a blade 200 disposed at least partially within an outer, hollow sheath 230 extending from the housing portion 102. In at least one embodiment, the horn 124 and blade 200 may be unitary and integrally formed from the same piece of material. In another embodiment, the horn 124 and blade 200 may be separate components that are attached together.

In various embodiments, the ultrasonic generator 12 may include an ultrasonic generator module 13 and a signal generator module 15. See FIG. 1. The ultrasonic generator module 13 and/or the signal generator module 15 each may be integrated with the ultrasonic generator 12 or may be provided as separate circuit modules electrically coupled to the ultrasonic generator 12 (shown in phantom to illustrate this option). In one embodiment, the signal generator module 15 may be formed integrally with the ultrasonic generator module 13. The ultrasonic generator 12 may comprise an input device 17 located on a front panel of the generator 12 console. The input device 17 may comprise any suitable device that generates signals suitable for programming the operation of the generator 12 in a known manner. Still with reference to FIG. 1, the cable 14 may comprise multiple electrical conductors, such as copper wires, for the application of electrical energy to positive (+) and negative (−) electrodes of an ultrasonic transducer assembly 114 as will be discussed in further detail below.

Various forms of ultrasonic generators, ultrasonic generator modules and signal generator modules are known. For example, such devices are disclosed in commonly owned U.S. patent application Ser. No. 12/503,770, entitled Rotating Transducer Mount For Ultrasonic Surgical Instruments, filed Jul. 15, 2007, now U.S. Patent Application Publication No. 2011-0015660, which is herein incorporated by reference in its entirety. Other such devices are disclosed in one or more of the following U.S. Patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

Figure 2:
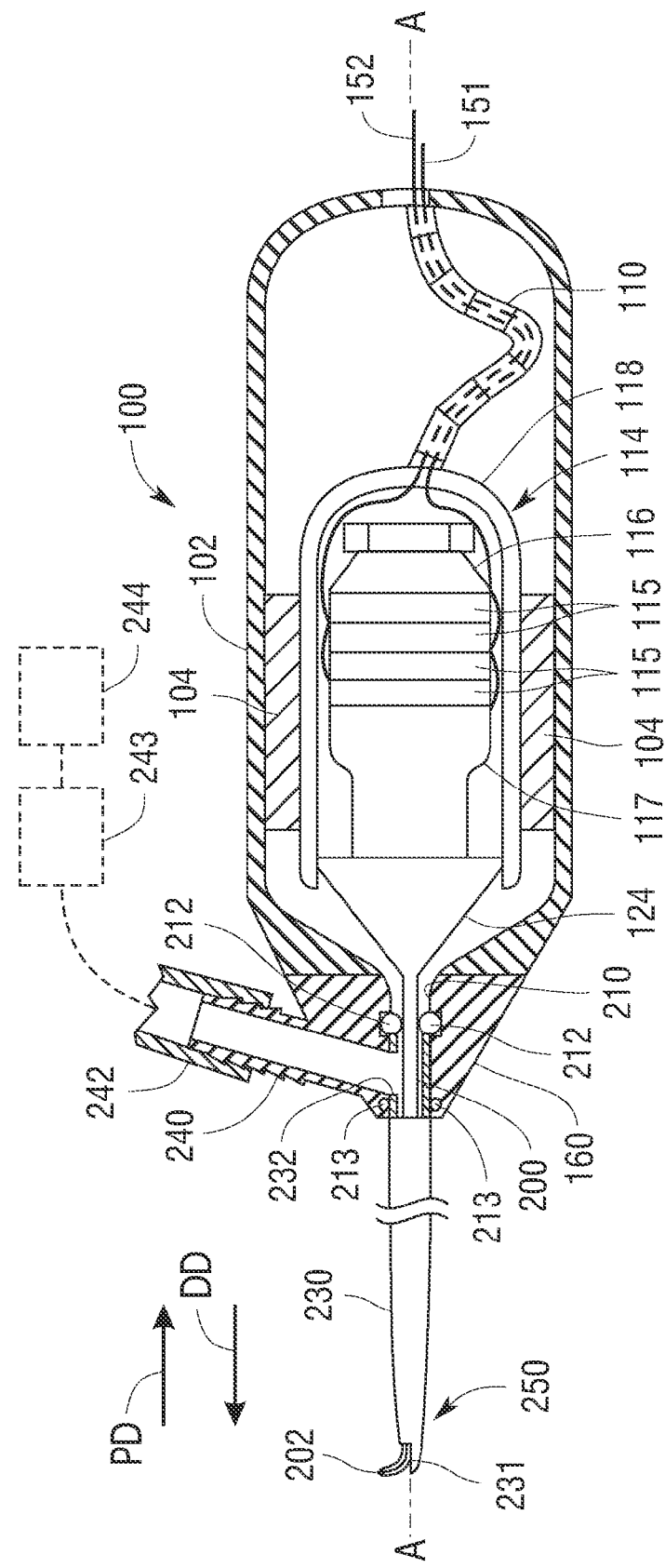
FIG. 2 is a partial cross-sectional view of a non-limiting embodiment of a handheld surgical instrument employing a blade and a hollow sheath.

As can be seen in FIG. 2, an ultrasonic surgical instrument 100 may comprise a housing 102 that houses the ultrasonic transducer assembly 114 and the horn 124. The transducer assembly 114 may be fixedly supported within the housing 102 by mounts 104. Extending from the horn 124 may be the blade 200, which passes through the hollow sheath 230 to a window or opening 231 defined therein. As shown in FIG. 2, a distal tip 202 of the blade 200 may be seen through the opening 231 at a distal portion 250 of the surgical instrument 100. The blade tip 202 and/or the distal portion 250 of the surgical instrument 100 may be considered the "end effector" of the instrument 100. As will be explained in more detail below, the blade 200 may cut tissue when the instrument is moved, relative to the tissue, in a proximal direction "PD" or a distal direction "DD" parallel to or coaxial with the hollow sheath's longitudinal axis A-A, in a direction transverse thereto, or in any direction therebetween. The housing 102 may be provided in two or more parts that are attached together by fasteners such as screws, snap features, etc. and/or by one or more adhesives and may be fabricated from, for example, polycarbonate, stainless steel, or other material.

Referring still to FIG. 2, the ultrasonic transducer assembly 114 may include a housing 118 that supports piezoelectric ultrasonic transducers 115 for converting electrical energy to mechanical energy that results in longitudinal vibrational motion of the ends of the transducers 115. The ultrasonic transducers 115 may comprise a stack of ceramic piezoelectric elements with a motion null point located at some point along the stack. The ultrasonic transducers 115 may be mounted between a proximal end piece 116 and a distal end piece 117. In addition, the horn 124 may be mounted to the distal end piece 117 at the null point on one side and to the blade 200 on the other side. As a result, the blade 200 will vibrate in the longitudinal direction at an ultrasonic frequency rate with the ultrasonic transducer assembly 114. The ends of the ultrasonic transducer assembly 114 achieve maximum motion with a portion of the stack constituting a motionless node, when the ultrasonic transducer assembly 114 is driven at maximum current at the transducer's resonant frequency. However, the current providing the maximum motion will vary with each instrument and is a value stored in the nonvolatile memory of the instrument so the system can use it.

The parts of the surgical instrument 100 may be designed such that the combination will oscillate at the same resonant frequency. In particular, the elements may be tuned such that the resulting length of each such element is one-half wavelength or a multiple thereof. Longitudinal back and forth motion is amplified as the diameter closer to the blade 200 of the acoustical mounting horn 124 decreases. Thus, the horn 124 as well as the blade 200 may be shaped and dimensioned so as to amplify blade motion and provide ultrasonic vibration in resonance with the rest of the acoustic system, which produces the maximum back and forth motion of the end of the acoustical mounting horn 124 close to the blade 200. A motion from 20 to 25 microns at the ultrasonic transducers 115 may be amplified by the horn 124 into blade movement of about 40 to 100 microns.

Referring briefly back to FIG. 1, when power is applied to the ultrasonic instrument 110 by a switch arrangement, the ultrasonic generator 12 may, for example, cause the blade 200 to vibrate longitudinally at approximately 55.5 kHz, and the amount of longitudinal movement will vary proportionately with the amount of driving power (current) applied, as adjustably selected by the user. When relatively high cutting power is applied, the blade 200 may be designed to move longitudinally in the range of about 40 to 100 microns at the ultrasonic vibrational rate. Such ultrasonic vibration of the blade 200 will generate heat as the blade contacts tissue, i.e., the acceleration of the blade 200 through the tissue converts the mechanical energy of the moving blade 200 to thermal energy in a very narrow and localized area. This localized heat creates a narrow zone of coagulation, which will reduce or eliminate bleeding in small vessels, such as those less than one millimeter in diameter. The cutting efficiency of the blade 200, as well as the degree of hemostasis, will vary with the level of driving power applied, the cutting rate or force applied by the surgeon to the blade, the nature of the tissue type, and the vascularity of the tissue.

Referring again to FIG. 2, the surgical instrument 100, and thus, the blade 200, may be grossly moved by a user, relative to a tissue to be cut. As used herein, the term "gross motion," and the like, is to be distinguished from "ultrasonic motion," and the like, that may be achieved by way of the ultrasonic transducer assembly. The term "gross motion" instead encompasses translational and rotational motion that is not solely generated by operation of the ultrasonic transducer assembly 114.

To provide the ultrasonic instrument 110 with power from the ultrasonic generator 12 (see FIG. 1), a flexible wire tray or a multiple-segment jointed protector 110 may be employed. As can be seen in FIG. 2, conductors 151, 152 are coupled to the ultrasonic transducer assembly 114 and extend out of the instrument through the housing 102. Further, the protector 110 may be attached to the instrument housing 102 at one end and to the transducer assembly housing 118 at the other end. The conductors 151, 152 may pass through one or more holes in the transducer assembly housing. Accordingly, ultrasonic signals from the ultrasonic generator 12 are transferred to the ultrasonic transducers 115 through the conductors 151, 152. The protector 110 may prevent the conductors 151, 152 from being damaged or pinched within the housing 102 when the instrument 100 is manufactured, for example.

Referring still to FIG. 2, various embodiments also include a distal nosepiece 160 that may be removably attached to the distal end of the housing 102 by fasteners and/or adhesives (not shown). The nosepiece 160 may be fabricated from, for example, stainless steel, aluminum or plastic. In various embodiments, the distal end 202 of the blade 200 extends through a hollow portion 210 of the nosepiece 160. The hollow sheath 230 may likewise extend through the hollow portion 210. The hollow portion 210 may include an annular groove in which a proximal seal 212 may be held against the end of the hollow sheath 230 and against the blade 200. The seal 212 may comprise, for example, a silicone o-ring, and/or a brazing or press fit seal, and serve to establish a substantially fluid-tight and/or airtight seal between the nosepiece 160, blade 200, and hollow sheath 230.

Also in various embodiments, the hollow sheath 230 may be coaxially aligned with the blade 200 and be attached to the hollow portion 210 of the nosepiece 160 by, for example, welding, press-fitting, threading, adhering with glue or other adhesive(s), etc. As can be seen in FIG. 2, a suction port 240 may be attached to the nosepiece 160 to communicate with a proximal hole 232 in the hollow sheath 230. A flexible tube 242 may be attached to the suction port 240 and communicate with a collection receptacle 243 that is coupled to a source of vacuum, generally depicted as 244. Thus, the hollow sheath 230 forms a suction path extending around the blade 200 that begins at the distal portion 250 of the outer sheath 230, such as at the opening 231, and goes out through the hole 232 to the suction port 240. Those of ordinary skill in the art will appreciate that alternate suction paths are also possible. Further, a distal seal 213, similar to proximal seal 212, may be held in the nosepiece 160 and may help further seal the hollow sheath 230 therein such that the suction path from the opening 231, through the sheath 230, out hole 232, and through the port 240 is maintained with minimal or no ingress of air from outside the aforementioned path. Alternatively, a suction port may be omitted from the nosepiece and the surgical instrument may operate without suction being applied to the opening 231.

Various embodiments of the surgical system 10 (see FIG. 1) provide the ability to selectively apply ultrasonic axial motion to the blade 200. If desired, the clinician may activate the ultrasonic transducer assembly 114 before or while cutting tissue with the blade 200. Frequency ranges for longitudinal ultrasonic motion may be on the order of, for example, 30-80 kHz. Similarly, the clinician may desire to move the instrument 100, and thus the blade 200, without activating the ultrasonic transducer assembly 114. Thus, gross motion may be applied to the blade 200, without the application of longitudinal ultrasonic motion thereto. In other applications, the clinician may desire to use the instrument 100 by both activating the ultrasonic transducer assembly 114 and by grossly moving the blade 200 with respect to the tissue to be cut. In such embodiments, the blade 200 will experience longitudinal ultrasonic motion from the transducer assembly 114 and gross motion from the clinician's movements. Moreover, those of ordinary skill in the art will readily appreciate that various embodiments of the surgical system 10 may be affectively employed in connection with arthroscopic as well as other surgical applications.

The surgical instrument 100 may have various distal portions. FIGS. 3 and 3A illustrate an example of a distal portion 250 of a non-limiting embodiment of a surgical instrument wherein like numbers previously used to describe the various embodiments disclosed above are used to designate like components. FIG. 3 is a perspective view of the surgical instrument's distal portion 250 and FIG. 3A is a cross-sectional view of the distal portion 250, taken along line 3A-3A in FIG. 3. In these embodiments, the surgical instrument, includes a thin, hollow sheath 230 including an opening 231, a blade 200 disposed at least partially within the hollow sheath 230 and extending through the opening 231, and at least one ultrasonic transducer (not shown, see transducers 115 in FIG. 2) operably coupled to the blade 200.

As can be seen in FIGS. 3 and 3A, in various embodiments, the blade 200 may comprise a distal tip 202 that projects away from the sheath's longitudinal axis A-A to facilitate the cutting of tissue. In more detail, the distal tip 202 may project a distance $L_1$ from the hollow sheath's longitudinal axis A-A. The distance $L_1$ may be of a sufficient amplitude to increase the blade's cutting effectiveness. In at least one embodiment, $L_1$ may be at least 0.25 inches. In another embodiment, $L_1$ may be less than or equal to 0.75 inches. In yet another embodiment, $L_1$ may be between and including 0.25 inches and 0.75 inches, in other words, $¼ \leq L_1 \leq ¾"$.

Further, the hollow sheath may be configured to expose various portions of the blade 200 to further facilitate tissue cutting for varying situations. For example, referring still to FIG. 3, in at least one embodiment, the sheath's opening 231 may define a plane that intersects the longitudinal axis A-A and that is not transverse to the longitudinal axis. As used herein, the term "transverse" means at a right angle to the longitudinal axis. In other words, the opening 231 is at an angle to the longitudinal axis, thereby exposing the blade only on one side 215 of the hollow sheath 230. In such embodiments, the backside 215 of the blade, that is the side 215 opposite the direction that the blade's tip 202 is projecting, may be shielded by the sheath 230 such that tissue is not unintentionally cut on that side 215. Additionally, as noted above, the sheath 230 may be thin and configured such that it is overmolded on the blade 230. In such embodiments, the clearance between the blade 200 and the sheath 230 (see FIG. 3A) may be minimized.

Alternatively, referring now to FIG. 4, in at least one embodiment, a hollow sheath 330 of a distal portion 350 of the surgical instrument may include an opening 331 that allows the blade 200 to project therethrough while exposing the backside 215 of the blade 200 to increase the cutting surface and/or edges available to cut tissue. In such embodiments, the opening 331 may define a first plane $P_1$ and a second plane $P_2$, which intersects the first plane, and the blade may extend through the first plane $P_1$. The first plane $P_1$ may be perpendicular to the longitudinal axis A-A and, as the second plane $P_2$ intersects the first plane $P_1$, the second plane $P_2$ may be at an angle to the first plane.

In another alternative embodiment, a hollow sheath 450 of a distal portion 450 of the surgical instrument may include an protective lip 433 that allows the blade 200 to be further protected from unintentionally cutting tissue. In more detail, while the blade may extend through the opening 431, it may still be desirable to prevent tissue from being cut on the blade's backside 215. Accordingly, the protective lip 433 may extend towards the tip 202 and away from the longitudinal axis A-A, thereby shielding a greater portion of the blade 200 than that shown in FIG. 3, for example.

Figure 6A:
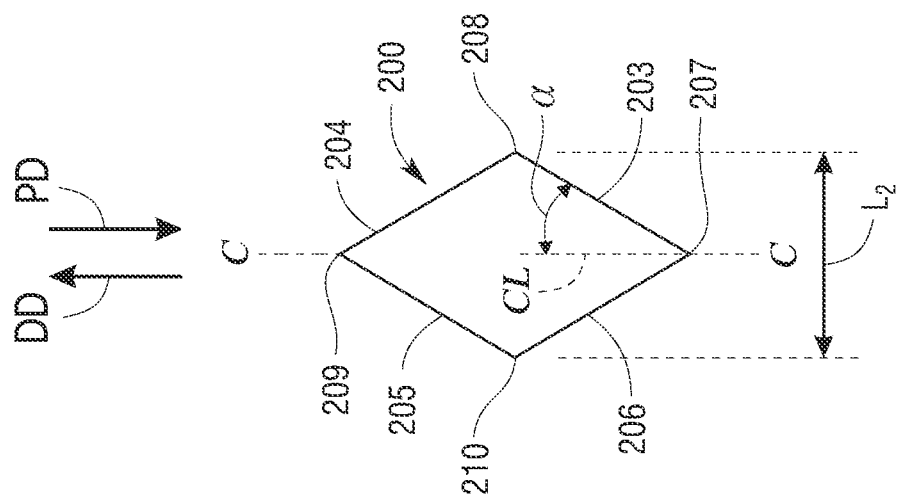
FIG. 6A is cross-sectional view of the blade of FIG. 6, taken along line 6A-6A; cross-hatching is omitted for clarity.
Figure 6:
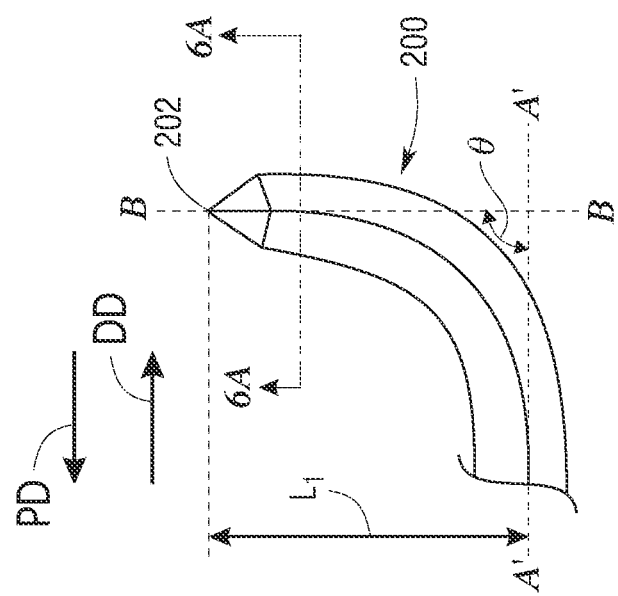
FIG. 6 is a side view of a distal portion of the blade of the surgical instrument of FIG. 2.

In various embodiments, referring now to FIGS. 6 and 6A, the blade 200 may include various features to enhance its cutting and/or coagulation ability. In more detail, FIG. 6 is a side view of a distal portion of the blade 200 and FIG. 6A is a cross-sectional view of the blade 200, taken along line 6A-6A. Note that cross-hatching is omitted for clarity in FIG. 6A. In at least one embodiment, as can be seen in FIG. 6, the blade 200 may be curved adjacent to the tip 202. Referring briefly back to FIG. 3, the blade 200 can be seen curving through the opening 231. The curved shape of the blade 200 may enable a smooth cut to be created along the blade 200, near the tip 202. More specifically, the blade may be curved a set amount such that the tip protrudes at a certain angle with respect to the hollow shaft's axis A-A (see FIG. 3). Focusing on FIG. 6, the blade 200 may define a first axis A'-A'. As can be seen in FIG. 3A, within the hollow shaft, the first axis A'-A' may be collinear or parallel to the hollow shaft's axis A-A. In any event, referring back to FIG. 6, the blade 200 may also define a second axis B-B through the tip 202. The second axis A-A may be tangent to the curve of the blade at or near the tip. The first and second axes may define an angle A that is equal to or greater than 60 degrees but equal to or less than 90 degrees. In other words, $60° \leq \theta \leq 90°$. Such tip angles may provide enhanced cutting function of the blade 200.

The shape of the tip 202 and/or cross-section of the blade may further increase the cutting ability of the blade 200. For example, in various embodiments, referring now to FIG. 6A, the blade 200 may increase the number of cutting surfaces it presents by employing a cross-sectional shape adjacent to the tip 202 that is a polygon. More specifically, in at least one embodiment, the polygonal cross-sectional shape may be a quadrilateral, and, even more specifically, a rhombus or equilateral parallelogram. Colloquially, the rhombus shape may be thought of as a diamond shape. Such shapes may allow for the blade to present sharp vertices, such as vertices 207, 208, 209, and 210 defined between sides 203, 204, 205, and 206, seen in FIG. 6A, which form part of the cutting edges of the blade. The degree of sharpness of a vertex, such as vertex 207, may be defined as follows. An angle α, defined between a side of the rhombus, such as side 203, and a centerline of the rhombus, such as centerline "CL," may be equal to or greater than 10 degrees but equal to or less than 25 degrees. In other words, $10° \leq \alpha \leq 25°$. By employing such sharp edges, as defined by the vertices of a rhombus shape, the blade 200 may reduce the need to be buffed.

Additionally, the cross-sectional shape of the blade may allow the blade to reduce drag through an aqueous or other fluid to better operate in such an environment. For example, in at least one embodiment, the cross-sectional rhombus shape may be longer in one direction and shorter in another. In more detail, the rhombus shape may be longer generally in the proximal and distal directions, PD and DD, respectively. Specifically, two of the vertices of the rhombus, vertices 207 and 209, may also define an axis C-C, see FIG. 6A, that is coplanar with the blade's longitudinal axis, see FIG. 3A. Accordingly, as the blade is moved in the proximal and distal directions, PD and DD, respectively, the drag experienced by the blade in a fluid environment is reduced. Further, the blade may be made thin such that the blade 200 has a width $L_2$, from vertex 208 to vertex 210, of 0.020 inches to 0.040 inches. In other words, $0.020" \leq L_2 \leq 0.040"$. In at least one embodiment, $L_2$ may be 0.030 inches.

In various embodiments, the tip 202 may also include a polygonal cross-section shape that tapers to a point. For example, in at least one embodiment, referring to FIG. 6, the tip may be pyramidal in shape. Accordingly, both the tip's pointed end and the edges of the tip's pyramidal shape may contribute enhanced cutting points and/or edges.

Additionally, in at least one embodiment, the blade 200 may be polygonal along its entire length, or, at least along a portion of the blade 200 that also resides within the hollow sheath 230, see FIG. 3A, for example. By using a uniform cross-section along at least a portion of the blade's length, manufacturing costs and resources may be reduced.

Figure 7:
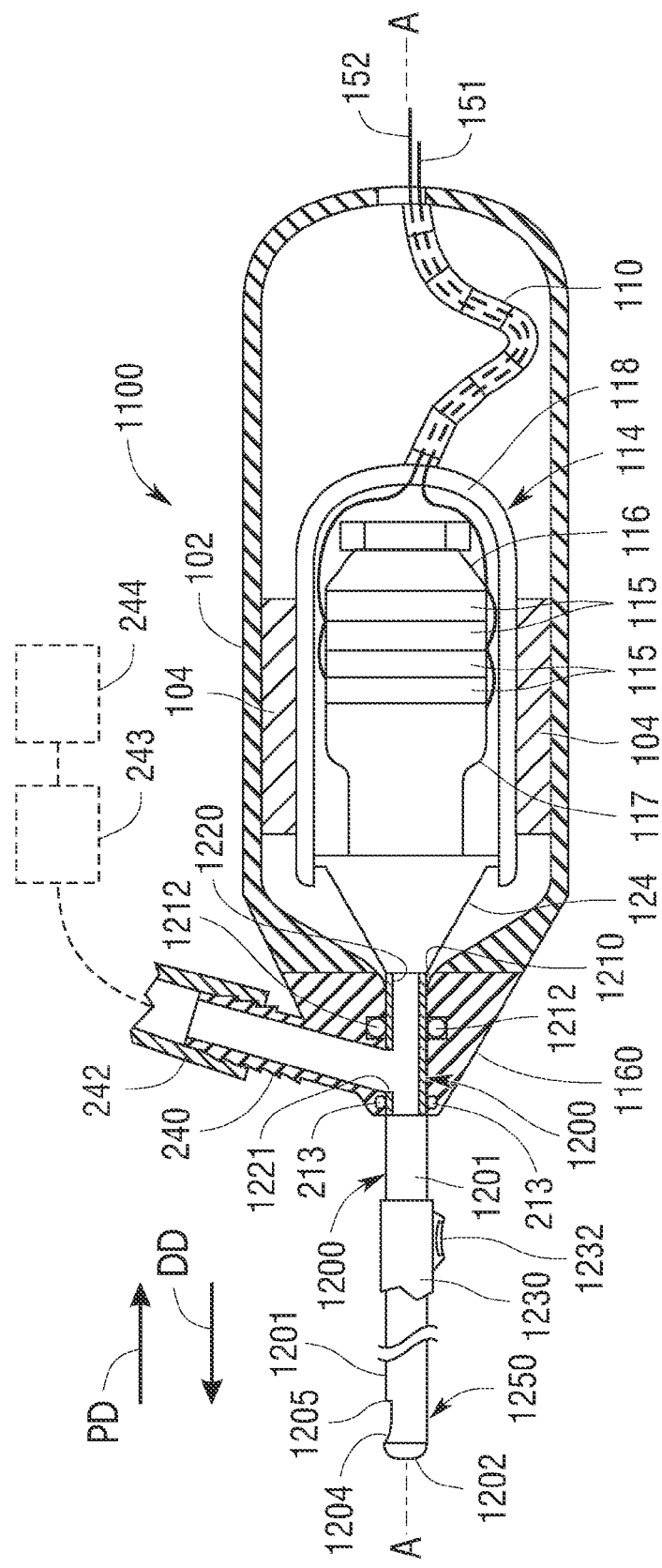
FIG. 7 is a partial cross-sectional view of a non-limiting embodiment of a handheld surgical instrument employing a blade with suction applied thereto.

Other blade and/or sheath configurations may be employed by a surgical instrument to achieve enhanced cutting and/or coagulation in a fluid environment. For example, in various embodiments, a surgical instrument may utilize suction to enhance cutting and removal of severed tissue from a surgical target. In more detail, FIGS. 7-11 illustrate another example of a non-limiting embodiment of a surgical instrument 1100 wherein like numbers previously used to describe the various embodiments disclosed above are used to designate like components. FIG. 7 is a partial cross-sectional view of a handheld surgical instrument 1100 employing a blade 1200 with suction applied thereto. The housing 102, transducer assembly 114, horn 124, and related components may be similar to that described above with respect to surgical instrument 100. At least one ultrasonic transducer, such as transducers 115 in the transducer assembly 114, may be operably coupled to the blade 1200 by the horn 124. The blade 1200 may define a longitudinal axis A-A, also similar to longitudinal axis A-A described above. Further, the blade 1200 may comprise a body 1201 that defines a lumen 1220 therein and includes a distal end 1202. Adjacent to the distal end 1202 may be an opening 1204 that communicates with the lumen 1202. Moreover, a first cutting edge 1205 may be positioned over the opening 1204. The first cutting edge 1205 may also project away from the longitudinal axis A-A, to further enhance cutting of tissue, as explained in more detail below.

The surgical instrument 1100 may further include a suction port 240 attached to or formed with nosepiece 1160. The suction port 240 may communicate with the lumen 1220 via a suction hole 1221 formed in the blade 1200, positioned within the nosepiece 1160, and aligned with the port 240. A flexible tube 242 may be attached to the suction port 240 and communicate with a collection receptacle 243 that is coupled to a source of vacuum 244. Thus, the blade 1200 may form a suction path extending through the blade 1200 that begins at a distal portion 1250 of the surgical instrument 1100, such as at the opening 1204, travels along at least a portion of lumen 1220, and goes out through the suction hole 1221 to the suction port 240. Those of ordinary skill in the art will appreciate that alternate suction paths are also possible. Further, a proximal seal 1212 and a distal seal 1213 may be held in annular grooves in the nosepiece 1160 around the port 240, and may help further seal the blade 1200 therein such that the suction path from the opening 1204, through the blade 1200, out hole 1221, and through the port 240 is maintained with minimal or no ingress of air from outside the aforementioned path. Accordingly, the blade 1200 is thereby configured to allow suction to be applied from the suction port 240 to the opening 1204.

Additionally, in at least one embodiment, an outer, hollow sheath 1230 may be employed that may function as a safety shield to cover at least the cutting edge 1205 and/or opening 1204 of the blade 1200 when introducing and/or removing the surgical instrument 1100 from a surgical site. The retractable hollow sheath 1230 may be movably mounted on the blade 1200 and may be selectively movable from a closed position substantially covering the opening 1204 and/or cutting edge 1205 to an open position exposing the opening 1204 (see FIG. 8). Such arrangement may cover the cutting edge 1205 and/or opening 1204 on the blade 1200 during insertion and removal of the blade 1200 adjacent vital nerves and other critical tissues. To facilitate movement of the hollow sheath 1230 on the blade 1200, a thumb control tab 1232 (FIG. 7) may be formed on the proximal end of the hollow sheath 1230 to enable the clinician to apply sliding actuation forces thereto.

In various embodiments, different blade configurations may be employed to enhance the cutting and evacuation of tissue from a surgical target. Focusing now on the distal portion of the surgical instrument 1250, best seen in FIG. 8, the blade may be tubular in shape. Further, the cutting edge 1205 can be seen positioned over the opening 1204 and projecting away from the blade's longitudinal axis A-A. In at least one such embodiment, focusing now on the front view of the distal portion 1250 provided by FIG. 9, the cutting edge can be seen defining an arc. Accordingly, tissue, such as vertebral disc tissue, may be cut smoothly and shaped along the arced cutting edge 1205.

Figure 10:
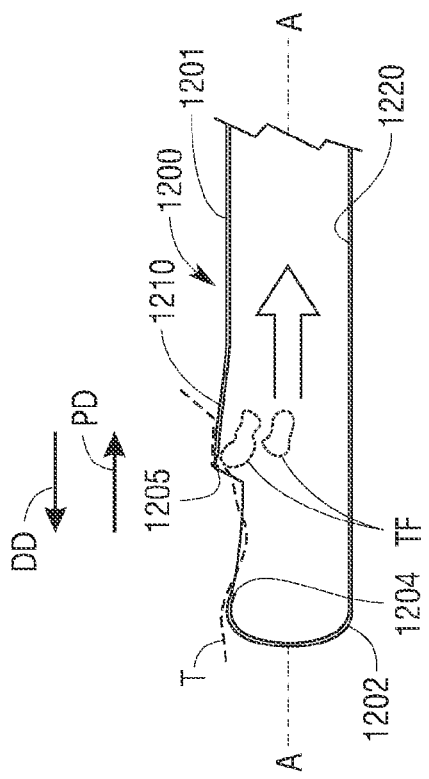
FIG. 10 is a side cross-sectional view of a distal portion of the blade of the surgical instrument of FIG. 7; the blade is shown cutting tissue to create tissue fragments that are subsequently evacuated by suction in a proximal direction.
Figure 11:
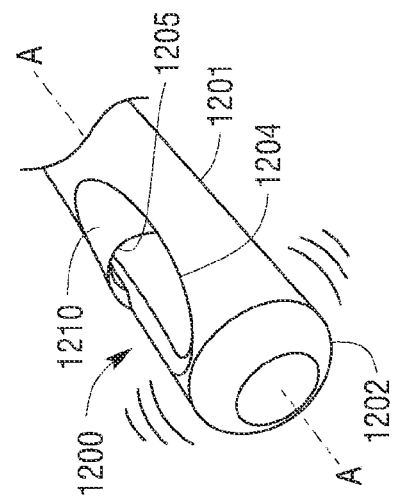
FIG. 11 is a perspective view of a distal portion of the blade of the surgical instrument of FIG. 7; the blade is shown vibrating with ultrasonic motions.
Figure 8:
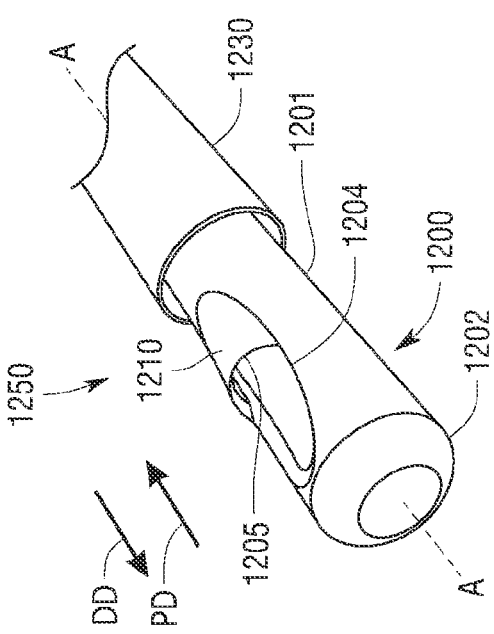
FIG. 8 is a perspective view of a distal portion of the surgical instrument of FIG. 7.
Figure 9:
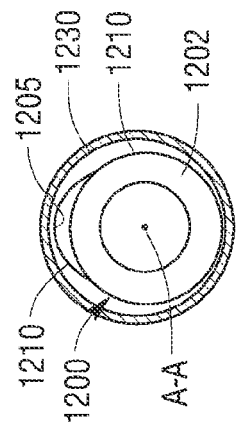
FIG. 9 is a front view of the distal portion of the surgical instrument of FIG. 7.

Further details regarding blade 1200 may be found by focusing on FIGS. 10-11. FIG. 10 shows a side cross-sectional view of a distal portion of the blade 1200 and FIG. 11 shows a perspective view of a distal portion of the blade 1200. The cutting edge 1205 may be defined by a cutting shroud 1210 that is integrally formed with the blade's body 1201 or otherwise attached thereto. As can be seen in FIG. 10, the shroud 1210 and cutting edge 1205 may project away from the longitudinal axis A-A and from the body 1201. Further, the cross-sectional shape of the shroud, again seen in FIG. 10, may project at an angle from the body 1201 to better present the cutting edge 1205 to tissue T. Also, as can be seen in FIG. 10, the cutting edge 1205 of the blade is shown cutting tissue "T" to create tissue fragments "TF" that are subsequently pulled in through opening 1204 and evacuated by suction in a proximal direction PD, as discussed above. The tissue may be cut when the blade 1200 is advanced in the distal direction DD such that the cutting edge 1205 imbeds itself against the tissue T or otherwise scrapes the tissue's surface. Alternatively, tissue may be sucked into the cutting edge 1205 by suction applied to the opening 1204. Further, with suction present, the tissue fragments TF may be cleared out of the surgical target area, thereby eliminating or reducing the need for repeated insertion and removal of the surgical instrument from a patient. Additionally, as illustrated in FIG. 11, the blade 1200 may vibrate with ultrasonic motions created by one or more ultrasonic transducers 115 (see FIG. 7) to further enhance the cutting edge's ability to severe and/or ablate tissue.

Focusing back on FIG. 7, in use, the clinician may activate the vacuum source 244 to cut and evacuate tissue. When a bleeder is encountered, the clinician may activate the ultrasonic transducer assembly 114 to send ultrasonic motions to the blade 1200 for coagulation purposes. For example, spinal fusion surgeries require the removal of disc material due to a variety of disease states. Often times this material is toughened and requires quite a bit of force with conventional instrumentation to break up the disc and remove its fragments. Once the disc material is removed, the end plates must be scraped to reveal fresh surfaces to promote fusion of the plates to the cage. The plates must also be shaped to provide a good fit with the type of cage being used. Conventional instrumentation generally requires high forces from the surgeon very close to critical structures.

Figure 12:
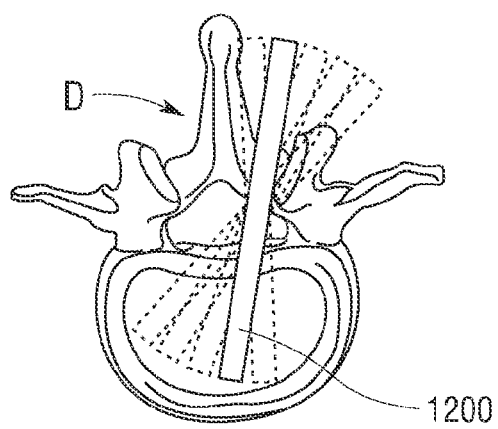
FIG. 12 illustrates use of the surgical instrument of FIG. 7 in connection with performing a discectomy.
Figure 13:
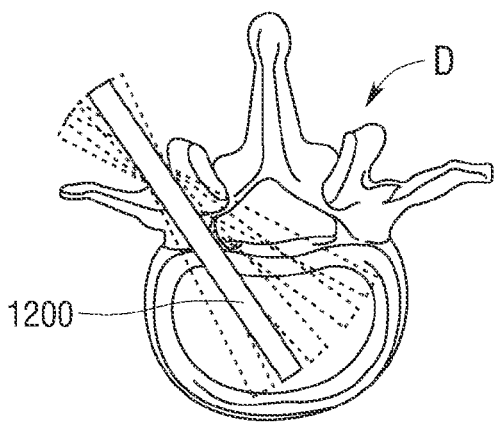
FIG. 13 depicts further use of the surgical instrument of FIG. 7 in connection with performing a discectomy.

Use of the above-described surgical instrument 1100 may be particularly advantageous when performing, for example, a discectomy as shown in FIGS. 12 and 13. As can be seen in those drawings, the blade 1200 may be inserted into the disc "D". The blade 1200 may be used to shave off small pieces of disc and suction them out. Such arrangement eliminates the need for repeated insertion/removal of surgical tools. The device may also be employed to prepare the vertebrae endplates. By incorporating suction through the blade 1200, ultrasonic motion to the blade 1200, and/or unique blade configurations, the amount of input force that a clinician must exert to prepare the endplates may be reduced. Similarly, the amount of external force required to break up and remove disc material may be lowered. Additionally, the number of instrument exchanges during a surgical procedure may be decreased.

Figure 14:
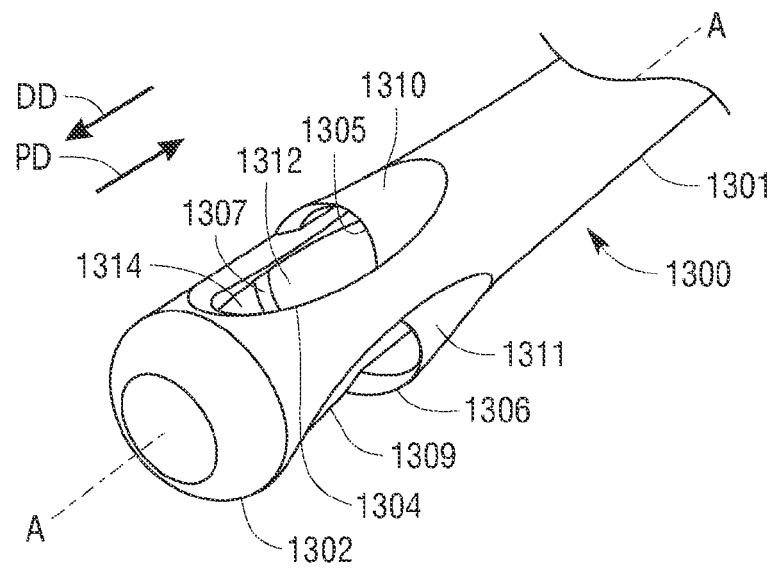
FIG. 14 is a perspective view of an alternative embodiment of the distal portion of the blade of the surgical instrument of FIG. 7.
Figure 15:
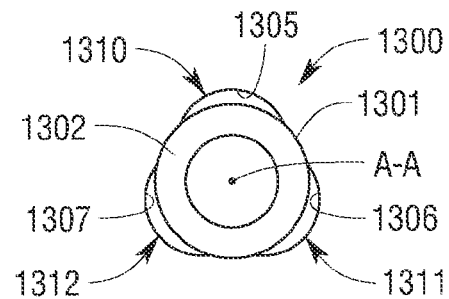
FIG. 15 is a front view of the distal portion of the blade of FIG. 12.

The surgical instrument 1100 may have various blades from that provided above. For example, FIG. 14 shows a perspective view of an alternative embodiment of a distal portion of a blade 1300 for the surgical instrument 1100 (see FIG. 7) and FIG. 15 shows a front view of the distal portion of the blade 1300. In at least one embodiment, the blade 1300 may be similar to the blade 1200 described above except that it may include more than one opening and/or cutting edge, which may be advantageously positioned on the blade. In more detail, the blade may define a longitudinal axis A-A and may comprise a distal end 1302, a lumen (not shown, see lumen 1220 in FIG. 7), and a first opening 1304 adjacent to the distal end 1302 and communicating with the lumen. The blade 1300 may include a first cutting edge 1305 positioned over the first opening 1304 and projecting away from the longitudinal axis A-A, similar to cutting edge 1204, described above. Further, the blade 1300 may also include a second opening 1309 that also communicates with the lumen and a second cutting edge 1306 positioned over the second opening 1309 and projecting away from the longitudinal axis A-A. The first opening 1304 and the second opening 1309 may both be at the same relative longitudinal position along the blade 1200. In other words, both openings 1304, 1309 may be the same distance from the distal end 1302, along longitudinal axis A-A, however, both openings 1304, 1309 may be at different angular positions along the blade's body 1301.

Adding more than one opening may increase the positions at which the blade 1300 may cut tissue. Accordingly, in at least one embodiment, the blade 1300 may further comprise a third opening 1307 to further enhance the cutting positions of the blade. In more detail, the third opening may also communicate with the lumen and be positioned at the same longitudinal position as the other openings 1304, 1309. A third cutting edge 1307 may be positioned over the third opening 1314 and may also project away from the longitudinal axis A-A. Each cutting edge 1305, 1306, 1307 may be defined by a cutting shroud 1310, 1311, 1312, respectively, which may be similar to shroud 1210 described above. Additionally, each of the openings 1304, 1309, 1314, the cutting edges 1305, 1306, 1307, and/or the shrouds 1310, 1311, 1312 may be symmetric about the longitudinal axis and positioned equidistant from one another. See, for example, FIG. 15.

Figure 16:
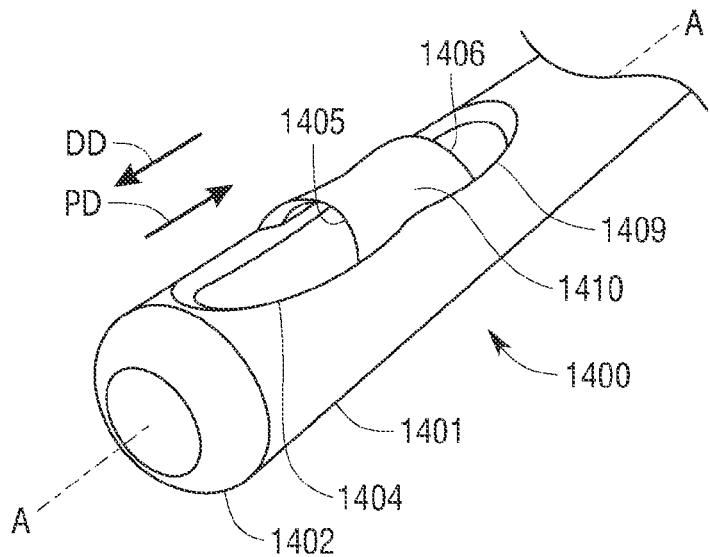
FIG. 16 is a perspective view of another alternative embodiment of the distal portion of the blade of the surgical instrument of FIG. 7.
Figure 17:
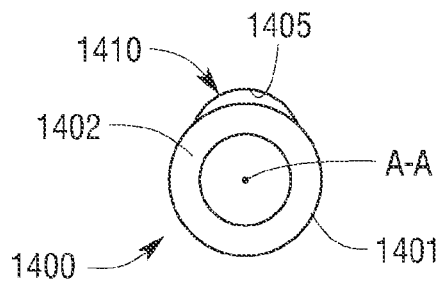
FIG. 17 is a front view of the distal portion of the blade of FIG. 14.
Figure 18:
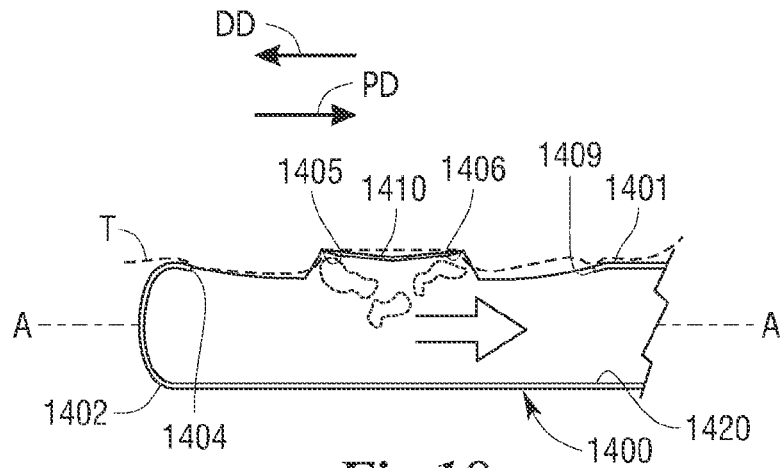
FIG. 18 is a side cross-sectional view of a distal portion of the blade of FIG. 14; the blade is shown cutting tissue to create tissue fragments that are subsequently evacuated by suction in a proximal direction.

While some of the above embodiments have shown a distal facing cutting edge or edges, the surgical instrument 1100 may include a blade that has a proximal facing cutting edge or edges. For example, FIG. 16 shows a perspective view of another alternative embodiment of a distal portion 1400 of a blade 1400 for the surgical instrument 1100 (see FIG. 7), FIG. 17 shows a front view of the distal portion of the blade 1400, and FIG. 18 shows a side cross-sectional view of a distal portion of the blade 1400 while the blade 1400 is cutting tissue T to create tissue fragments TF that are subsequently evacuated by suction in a proximal direction, similar to that described above. In at least one embodiment, the blade 1400 may be similar to the blade 1200 described above except that it may include more than one opening and/or cutting edge, which may be juxtaposed to one another.

In more detail, the blade may define a longitudinal axis A-A and may comprise a distal end 1402, a lumen 1420, and a first opening 1404 adjacent to the distal end 1402 and communicating with the lumen 1420. The blade 1400 may include a first cutting edge 1405 positioned over the first opening 1404 and projecting away from the longitudinal axis A-A, similar to cutting edge 1204, described above. Further, the blade 1400 may also include a second opening 1409 that is proximal to the first opening and/or to the first cutting edge 1405. The second opening 1409 may also communicate with the lumen 1420. Further, a second cutting edge 1406 may be positioned over the second opening 1409 and project away from the longitudinal axis A-A. The first opening 1404 and the second opening 1409 may be at different relative longitudinal positions along the blade 1400 but may both be at the same angular position along the blade's body 1401. In other words, the openings 1404, 1409 may be on the same side of the blade 1400. In at least one embodiment, the cutting edges 1405, 1406 may be defined by the same cutting shroud 1410. In such embodiments, the shroud 1410 may be positioned over both openings 1404, 1409.

Referring to FIG. 18, the tissue may be cut when the blade 1400 is advanced in the distal direction DD such that the first, distal-facing cutting edge 1405 imbeds itself against the tissue T or otherwise scrapes the tissue's surface. Additionally, the tissue may be cut when the blade 1400 is retracted in the proximal direction such that the second, proximal-facing cutting edge 1406 imbeds itself against the tissue T or otherwise scrapes the tissue's surface. Alternatively, tissue may be sucked into one or more of the cutting edges 1405, 1406 by suction applied to the openings 1404, 1409, as described above. Further, with suction present, tissue fragments TF may be cleared out of the surgical target area, thereby eliminating or reducing the need for repeated insertion and removal of the surgical instrument from a patient. Additionally, the blade 1400 may vibrate with ultrasonic motions created by one or more ultrasonic transducers 115 (see FIG. 7) to further enhance the cutting edge's ability to severe and/or ablate tissue.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Sterilization can also be done by any number of ways known to those skilled in the art including beta or gamma radiation, ethylene oxide, and/or steam.

In various embodiments, an ultrasonic surgical instrument can be supplied to a surgeon with a waveguide and/or end effector already operably coupled with a transducer of the surgical instrument. In at least one such embodiment, the surgeon, or other clinician, can remove the ultrasonic surgical instrument from a sterilized package, plug the ultrasonic instrument into a generator, as outlined above, and use the ultrasonic instrument during a surgical procedure. Such a system can obviate the need for a surgeon, or other clinician, to assemble a waveguide and/or end effector to the ultrasonic surgical instrument. After the ultrasonic surgical instrument has been used, the surgeon, or other clinician, can place the ultrasonic instrument into a sealable package, wherein the package can be transported to a sterilization facility. At the sterilization facility, the ultrasonic instrument can be disinfected, wherein any expended parts can be discarded and replaced while any reusable parts can be sterilized and used once again. Thereafter, the ultrasonic instrument can be reassembled, tested, placed into a sterile package, and/or sterilized after being placed into a package. Once sterilized, the reprocessed ultrasonic surgical instrument can be used once again.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a hollow sheath including an outer perimeter and an opening, wherein the hollow sheath defines a longitudinal axis;
   a blade disposed at least partially within the hollow sheath and extending through the opening, wherein the blade comprises a tip and a cross-sectional shape adjacent to the tip that is a polygon, and wherein the tip projects away from the longitudinal axis and radially extends beyond the outer perimeter; and
   at least one ultrasonic transducer operably coupled to the blade.

2. The surgical instrument of claim 1, wherein the opening defines a plane that intersects the longitudinal axis and that is not transverse to the longitudinal axis.

3. The surgical instrument of claim 1, wherein the opening defines a first plane and a second plane intersecting the first plane, wherein the blade extends through the first plane.

4. The surgical instrument of claim 1, wherein the tip curves towards a first side of the blade, wherein the hollow sheath further comprises a protective lip extending along a second side of the blade and towards the tip, and wherein the second side is substantially opposite to the first side.

5. The surgical instrument of claim 1, wherein the blade further includes a tip that is at least 0.25 inches away from the longitudinal axis but not more than 0.75 inches away from the longitudinal axis.

6. The surgical instrument of claim 1, wherein the blade is curved adjacent to the tip, wherein the blade defines a first axis within the hollow sheath and a second axis through the tip, wherein the first and second axes define an angle, and wherein the angle is equal to or greater than 60 degrees but equal to or less than 90 degrees.

7. The surgical instrument of claim 1, wherein the tip comprises a pyramidal shape.

8. The surgical instrument of claim 1, wherein the polygon is a quadrilateral.

9. The surgical instrument of claim 8, wherein the quadrilateral is a rhombus.

10. The surgical instrument of claim 9, wherein the rhombus defines an angle between a side of the rhombus and a centerline of the rhombus, wherein the angle is equal to or greater than 10 degrees but equal to or less than 25 degrees.

11. The surgical instrument of claim 9, wherein the rhombus comprises four vertices, wherein two of the vertices define an axis that is coplanar with the blade's longitudinal axis.

12. The surgical instrument of claim 1, further comprising:
   a suction port communicating with the hollow sheath, wherein the hollow sheath is configured to allow suction to be applied from the suction port to the opening.

13. The surgical instrument of claim 1, wherein the tip tapers to a point, and wherein the polygon comprises sharp vertices.

14. A surgical instrument, comprising:
   a hollow sheath including an opening, wherein the hollow sheath defines a longitudinal axis;
   a blade disposed at least partially within the hollow sheath and extending through the opening, wherein the blade comprises:
      a pyramidal end comprising a plurality of planar faces, a plurality of non-rounded corners, and a pointed tip, wherein the pyramidal end projects away from the longitudinal axis; and
      a cross-sectional shape adjacent to the pyramidal end that is a polygon; and
   at least one ultrasonic transducer operably coupled to the blade.

15. The surgical instrument of claim 14, wherein the pointed tip curves towards a first side of the blade, wherein the hollow sheath further comprises a protective lip extending along a second side of the blade and towards the tip, and wherein the second side is substantially opposite to the first side.

16. The surgical instrument of claim 14, wherein the polygon comprises a parallelogram, and wherein the parallelogram comprises non-rounded corners.

17. A surgical instrument, comprising:
   a hollow sheath including an opening, wherein the hollow sheath defines a longitudinal axis;
   a blade disposed at least partially within the hollow sheath and extending through the opening, wherein the blade comprises a tip and a cross-sectional shape adjacent to the tip that is a quadrilateral, wherein the tip projects away from the longitudinal axis, and wherein the quadrilateral comprises pointed vertices; and
   at least one ultrasonic transducer operably coupled to the blade.

18. The surgical instrument of claim 17, wherein the tip tapers to a point.

19. The surgical instrument of claim 18, wherein the tip comprises a pyramidal shape.

20. The surgical instrument of claim 17, wherein the quadrilateral is a rhombus.

21. The surgical instrument of claim 20, wherein the quadrilateral defines an angle between adjacent sides, and wherein the angle is equal to or greater than 20 degrees but equal to or less than 50 degrees.

* * * * *

UNITED STATES PATENT AND TRADEMARK OFFICE
CERTIFICATE OF CORRECTION

PATENT NO. : 8,579,928 B2
APPLICATION NO. : 12/703885
DATED : November 12, 2013
INVENTOR(S) : Robertson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 442 days.

Signed and Sealed this
Twenty-first Day of April, 2015

Michelle K. Lee
*Director of the United States Patent and Trademark Office*